(12) United States Patent  
Chattopadhyaya

(10) Patent No.: US 8,461,124 B2  
(45) Date of Patent: Jun. 11, 2013

(54) FIVE- AND SIX-MEMBERED CONFORMATIONALLY LOCKED 2',4'-CARBOCYCLIC RIBO-THYMIDINES FOR THE TREATMENT OF INFECTIONS AND CANCER

(76) Inventor: Jyoti Chattopadhyaya, Uppsala (SE)

( * ) Notice: Subject to any disclaimer, the term of this patent is extended or adjusted under 35 U.S.C. 154(b) by 541 days.

(21) Appl. No.: 12/531,394

(22) PCT Filed: Mar. 11, 2008

(86) PCT No.: PCT/SE2008/050268  
§ 371 (c)(1),  
(2), (4) Date: Sep. 15, 2009

(87) PCT Pub. No.: WO2008/111908  
PCT Pub. Date: Sep. 18, 2008

(65) Prior Publication Data  
US 2010/0087387 A1 Apr. 8, 2010

(30) Foreign Application Priority Data  
Mar. 15, 2007 (SE) ...................... 0700649

(51) Int. Cl.  
*C12N 15/46* (2006.01)  
*A01N 43/04* (2006.01)  
*A61K 31/70* (2006.01)  
*C07H 21/02* (2006.01)  
*C07H 21/04* (2006.01)  
*C07H 21/00* (2006.01)  
*C07H 19/10* (2006.01)  
*C07H 19/048* (2006.01)  
*C07H 19/167* (2006.01)  
*C07H 19/173* (2006.01)  
*C07H 19/00* (2006.01)

(52) U.S. Cl.  
USPC ............... 514/44 A; 514/45; 514/46; 514/49; 514/50; 514/51; 536/23.1; 536/24.5; 536/25.34; 536/26.8; 536/27.6; 536/27.81; 536/28.5; 536/28.52; 536/28.53; 536/28.55

(58) Field of Classification Search  
None  
See application file for complete search history.

(56) References Cited

U.S. PATENT DOCUMENTS  
6,268,490 B1 7/2001 Imanishi et al.

FOREIGN PATENT DOCUMENTS  
WO WO 2004/035819 A2 4/2004  
WO WO 2005/020885 A2 3/2005

OTHER PUBLICATIONS

Makoto Koizumi, "ENA® oligonucleotides as therapeutics," *Curr. Opin. Mol. Ther.*, 2006, vol. 8, pp. 144-149.

PCT International Search Report issued by PCT International Searching Authority and mailed May 30, 2008 in connection with the PCT International Application No. PCT/SE2008/050268 (8 pages).

(Continued)

*Primary Examiner* — Lawrence E Crane

(57) ABSTRACT

Conformationally locked 2',4'-carbocylic nucleosides with improved thermal and nuclease stability are disclosed. Oligonucleotides incorporating the locked nucleosides, and methods of treating disease states, are also disclosed.

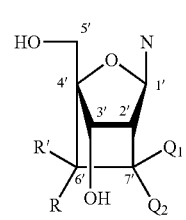

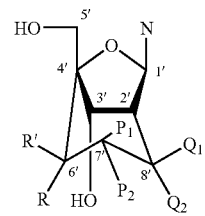

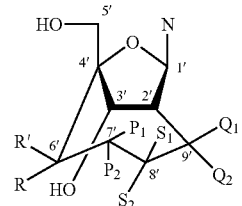

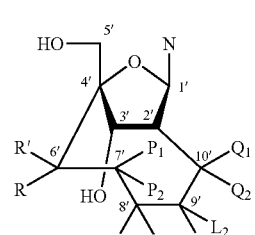

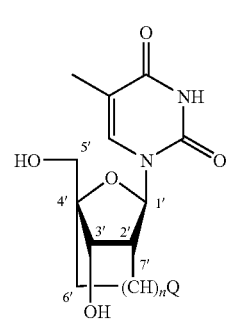

5 Claims, 9 Drawing Sheets

OTHER PUBLICATIONS

Figure 1:
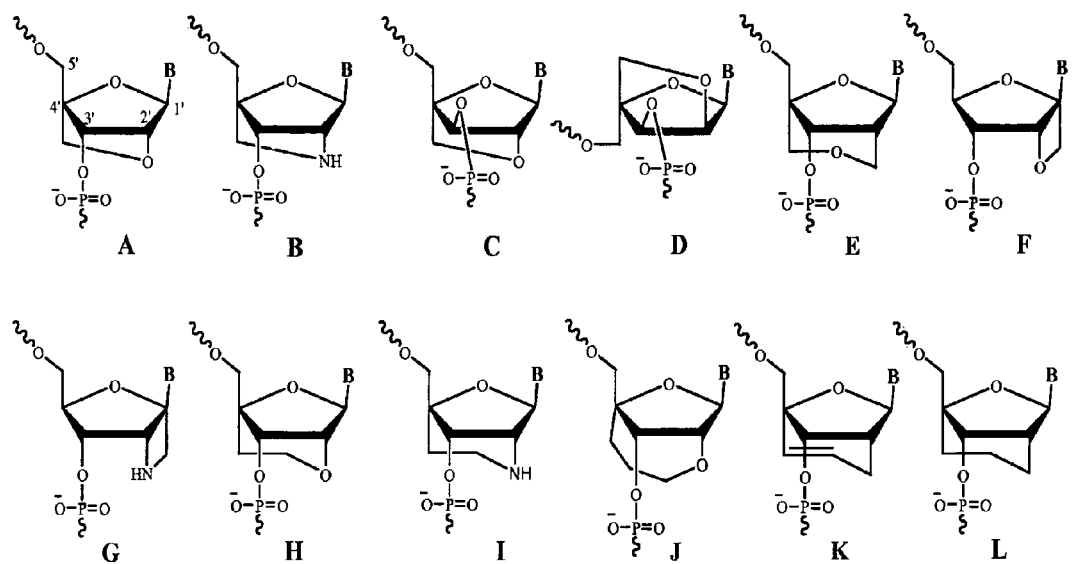

PCT Written Opinion of the International Searching Authority mailed May 30, 2008 in connection with the PCT International Application No. PCT/SE2008/050268 (11 pages).

Satoshi Obika et al., "Synthesis of 2'-$O$,4'-$C$-methyleneuridine and -cytidine. noble bicyclic Nucleosides having a fixed C3'-endo sugar puckering," *Tetrahedron. Letters*, vol. 38, No. 50, 1997, pp. 8735-8738.

Sanjay K. Singh et al., "LNA (locked nucleic acids): synthesis and high-affinity nucleic acid recognition," *Chemical Communications*, 1998, p. 455.

Claes Wahlestedt et al., "Potent and nontoxic antisense oligonucleotides containing locked nucleic acids," *PNAS (Proceedings of the National Academy of Sciences)*, vol. 97, No. 10, May 9, 2000, pp. 5633-5638.

Koji Morita et al., "2'-$O$,4'-$C$-ethylene-bridged nucleic acids (ENA) : highly nuclease-resistant and thermodynamically stable oligonucleotides for antisense drug," *Bioorganic & Medicinal Chemistry Letters*, vol. 2, 2002, pp. 73-76.

Nanna Albaek et al., "Analogues of a locked nucleic acid with three-carbon 2' , 4'-linkage : synthesis by ring-closing metathesis and influence on nucleic acid duplex stability and structure," *Journal of Organic Chemistry*, vol. 71, No. 20, 2006, pp. 7731-7740.

Oommen P. Varghese et al., "Conformationally constrained 2'-$N$,4'-$C$-ethylene-bridged thymidine (Aza-ENA-T): synthesis, structure, physical, and biochemical studies of Aza-ENA-T-modified oligonucleotides," *Journal of the American Chemical Society*, vol. 128, No. 47, 2006, pp. 15173-15187.

Torsten Bryld et al., "Synthesis and antiviral evaluation of novel conformationally locked nucleosides and masked 5'-phosphate derivatives thereof," *Journal of the Chemical Society, Perkin Transactions 1*, vol. 14, 2002, pp. 1655-1662.

Jacob Ravn et al., "Design, synthesis, and biological evaluation of LNA nucleosides as adenosine $A_3$ receptor ligands," *Bioorganic and Medicinal Chemistry*, vol. 15, No. 16, 2007, pp. 5440-5447.

Puneet Srivastava et al., "Five- and six-membered conformationally locked 2',4'-carbocyclic *ribo*-thymidines: Synthesis, structure, and biochemical studies," *Journal of the American Chemical Society*, vol. 129, No. 26, 2007, pp. 8362-8379.

Paul C. Zamecnik, et al., "Inhibition of rous sarcoma virus replication and cell transformation by a specific oligodeoxynucleotide," *Proc. Natl. Acad. Sci. USA*, Jan. 1978, vol. 75, No. 1, pp. 280-284.

Stanley T. Crooke, "Progress in antisense technology," *Annu. Rev. Med.*, 2004, vol. 55, pp. 61-95.

Sabrina Buchini, et al., "Recent improvements in antigene technology," *Curr. Opin. Chem. Biol.*, 2003, vol. 7, pp. 717-726.

Mary K. Montgomery, et al., "RNA as a target of double-stranded RNA-mediated genetic interference in *Caenorhabditis elegans*," *Proc. Natl. Natl. Acad. Sci. USA*, Dec. 1998, vol. 95, pp. 15502-15507.

Jens Kurreck, "Antisense technologies: Improvement through novel chemical modifications," *Eur. J. Biochem.*, 2003, vol. 270, pp. 1628-1644.

Susan M. Freier, et al., "The ups and downs of nucleic acid duplex stability: structure-stability studies on chemically-modified DNA:RNA duplexes," *Nucleic Acids Res.*, 1997, vol. 25, No. 22, pp. 4429-4443.

F. Eckstein, "Nucleoside phosphorothioates," *Annu. Rev. Biochem.*, 1985, vol. 54., pp. 367-402.

Jon T. Holmlund, "Applying antisense technology: Affinitak™ and other antisense oligonucleotides in clinical development," *Ann. N.Y. Acad. Sci.*, 2003, vol. 1002, pp. 244-251.

Christian J. Leumann, "DNA analogies: From supramolecular principles to biological properties," *Bioorg. & Med. Chem.*, 2002, vol. 10, pp. 841-854.

Ralph Steffens, et al., "Preparation of [(5'$R$,6'$R$)-2'-Deoxy-3',6'-ethano-5',6'methano-β-D-ribofuranosyl]thymine and -adenine, and the corresponding phosphoramidites for oligonucleotide synthesis," *Helv. Chim. Acta.*, 1997, vol. 80, p. 2426-2439.

Jesper Wengel, "Synthesis of 3'-$C$-and 4'-$C$-branched oligodeoxynucleotides and the development of locked nucleic acid (LNA)," *Acc. Chem. Res.*, 1999, vol. 32, pp. 301-310.

Alexei A. Koshkin, et al., "LNA (locked nucleic acids): synthesis of the adenine, cytosine, guanine, 5-methylcytosine, thymine and uracil bicyclonucleoside monomers, oligomerisation, and unprecedented nucleic acid recognition," *Tetrahedron*, 1998, vol. 54, pp. 3607-3630.

Koji Morita, et al., "Synthesis and properties of 2'-$O$, 4'-$C$-ethylene-bridged nucleic acids (ENA) as effective antisense oligonucleotides," *Bioorg. & Med. Chem.*, 2003 vol. 11, pp. 2211-2226.

Sanjay K. Singh et al., "Synthesis of 2'-amino-LNA: a novel conformationally restricted high-affinity oligonucleotide analogue with a handle," *J. Org. Chem.*, 1998, vol. 63, pp. 10035-10039.

Pushpangadan I. Pradeepkumar, "Synthesis, physicochemical and biochemical studies of 1',2'-oxetane constrained adenosine and guanosine modified oligonucleotides, and their comparison with those of the corresponding cytidine and thymidine analogues," *J. Am. Chem. Soc.*, 2004, vol. 126, No. 37, pp. 11484-11499.

Dmytro Honcharenko, et al., "Synthesis and structure of novel conformationally constrained 1',2'-azetidine-fused bicyclic pyrimidine nucleosides: their incorporation into oligo-DNAs and thermal stability of the heteroduplexes," *J. Org. Chem.*, 2006, vol. 71, pp. 299-314.

B. Ravindra Babu, et al., "XNA (*xylo* nucleic acid): A summary and new derivatives," *Eur. J. Org. Chem.*, 2005, pp. 2297-2321.

Vivek K. Rajwanshi, et al., "The eight stereoisomers of LNA (locked nucleic acid) : a remarkable family of strong RNA binding molecules," *Angew. Chem. Int. Ed.*, 2000, vol. 39, No. 9, pp. 1656-1659.

Koji Morita, et al., "Down-regulation of VEGF mRNA expression by 2'-$O$,4'-$C$-ethylene-bridged nucleic acid (ENA) antisense oligonucleotides and investigation of non-target gene expression," *Nucleic Acids Res. Sup.* No. 2, 2002, pp. 99-100.

Koji Morita, et al., "2'-$O$,4'-$C$-ethylene-bridged nucleic acid (ENA™) for effective antisense formation," *Nucleosides, Nucleotides and Nucleic Acids*, 2003, vol. 22, Nos. 5-8, pp. 1619-1621.

Peter Bakuzis, et al., "Total synthesis of sativene and copacamphene via a free radical cyclization," *J. Org. Chem.*, 1976, vol. 41, No. 20, pp. 3261-3264.

```
                        SEQUENCE LISTING

<160> NUMBER OF SEQ ID NOS: 17

<210> SEQ ID NO 1
<211> LENGTH: 15
<212> TYPE: DNA
<213> ORGANISM: Simian virus 40
<300> PUBLICATION INFORMATION:
<308> DATABASE ACCESSION NUMBER: NC_001669
<309> DATABASE ENTRY DATE: 2011-03-09
<313> RELEVANT RESIDUES IN SEQ ID NO: (5005)..(5019)

<400> SEQUENCE: 1
cttcattttt tcttc                                                     15

<210> SEQ ID NO 2
<211> LENGTH: 15
<212> TYPE: DNA
<213> ORGANISM: Simian virus 40
<220> FEATURE:
<221> NAME/KEY: misc_feature
<222> LOCATION: (13)..(13)
<223> OTHER INFORMATION: n is a, c, g, or t

<400> SEQUENCE: 2
cttcattttt tcntc                                                     15

<210> SEQ ID NO 3
<211> LENGTH: 15
<212> TYPE: DNA
<213> ORGANISM: Simian virus 40
<220> FEATURE:
<221> NAME/KEY: misc_feature
<222> LOCATION: (10)..(10)
<223> OTHER INFORMATION: n is a, c, g, or t

<400> SEQUENCE: 3
cttcattttn tcttc                                                     15

<210> SEQ ID NO 4
```

```
<211> LENGTH: 15
<212> TYPE: DNA
<213> ORGANISM: Simian virus 40
<220> FEATURE:
<221> NAME/KEY: misc_feature
<222> LOCATION: (8)..(8)
<223> OTHER INFORMATION: n is a, c, g, or t

<400> SEQUENCE: 4
cttcattntt tcttc                                                    15

<210> SEQ ID NO 5
<211> LENGTH: 15
<212> TYPE: DNA
<213> ORGANISM: Simian virus 40
<220> FEATURE:
<221> NAME/KEY: misc_feature
<222> LOCATION: (6)..(6)
<223> OTHER INFORMATION: n is a, c, g, or t

<400> SEQUENCE: 5
cttcantttt tcttc                                                    15

<210> SEQ ID NO 6
<211> LENGTH: 15
<212> TYPE: DNA
<213> ORGANISM: Simian virus 40
<220> FEATURE:
<221> NAME/KEY: misc_feature
<222> LOCATION: (13)..(13)
<223> OTHER INFORMATION: n is a, c, g, or t

<400> SEQUENCE: 6 cttcatttttt tcntc                                                   15

<210> SEQ ID NO 7
<211> LENGTH: 15
<212> TYPE: DNA
<213> ORGANISM: Simian virus 40
<220> FEATURE:
<221> NAME/KEY: misc_feature
<222> LOCATION: (10)..(10)
<223> OTHER INFORMATION: n is a, c, g, or t

<400> SEQUENCE: 7
cttcattttn tcttc                                                    15

<210> SEQ ID NO 8
<211> LENGTH: 15
<212> TYPE: DNA
<213> ORGANISM: Simian virus 40
<220> FEATURE:
<221> NAME/KEY: misc_feature
<222> LOCATION: (8)..(8)
<223> OTHER INFORMATION: n is a, c, g, or t

<400> SEQUENCE: 8
cttcattntt tcttc                                                    15

<210> SEQ ID NO 9
<211> LENGTH: 15
<212> TYPE: DNA
<213> ORGANISM: Simian virus 40
<220> FEATURE:
<221> NAME/KEY: misc_feature
<222> LOCATION: (6)..(6)
<223> OTHER INFORMATION: n is a, c, g, or t

<400> SEQUENCE: 9
```

```
cttcantttt tcttc                                                    15

<210> SEQ ID NO 10
<211> LENGTH: 15
<212> TYPE: DNA
<213> ORGANISM: Simian virus 40
<220> FEATURE:
<221> NAME/KEY: misc_feature
<222> LOCATION: (13)..(13)
<223> OTHER INFORMATION: n is a, c, g, or t

<400> SEQUENCE: 10
cttcattttt tcntc                                                    15

<210> SEQ ID NO 11
<211> LENGTH: 15
<212> TYPE: DNA
<213> ORGANISM: Simian virus 40
<220> FEATURE:
<221> NAME/KEY: misc_feature
<222> LOCATION: (10)..(10)
<223> OTHER INFORMATION: n is a, c, g, or t

<400> SEQUENCE: 11
cttcattttn tcttc                                                    15

<210> SEQ ID NO 12
<211> LENGTH: 15
<212> TYPE: DNA
<213> ORGANISM: Simian virus 40
<220> FEATURE:
<221> NAME/KEY: misc_feature
<222> LOCATION: (8)..(8)
<223> OTHER INFORMATION: n is a, c, g, or t

<400> SEQUENCE: 12
cttcattntt tcttc                                                    15

<210> SEQ ID NO 13
<211> LENGTH: 15
<212> TYPE: DNA
<213> ORGANISM: Simian virus 40
<220> FEATURE:
<221> NAME/KEY: misc_feature
<222> LOCATION: (6)..(6)
<223> OTHER INFORMATION: n is a, c, g, or t

<400> SEQUENCE: 13
cttcantttt tcttc                                                    15

<210> SEQ ID NO 14
<211> LENGTH: 15
<212> TYPE: DNA
<213> ORGANISM: Simian virus 40
<220> FEATURE:
<221> NAME/KEY: misc_feature
<222> LOCATION: (13)..(13)
<223> OTHER INFORMATION: n is a, c, g, or t

<400> SEQUENCE: 14
cttcattttt tcntc                                                    15

<210> SEQ ID NO 15
<211> LENGTH: 15
<212> TYPE: DNA
<213> ORGANISM: Simian virus 40
<220> FEATURE:
<221> NAME/KEY: misc_feature
<222> LOCATION: (10)..(10)
```

```
<223> OTHER INFORMATION: n is a, c, g, or t

<400> SEQUENCE: 15
cttcattttn tcttc                                                           15

<210> SEQ ID NO 16
<211> LENGTH: 15
<212> TYPE: DNA
<213> ORGANISM: Simian virus 40
<220> FEATURE:
<221> NAME/KEY: misc_feature
<222> LOCATION: (8)..(8)
<223> OTHER INFORMATION: n is a, c, g, or t

<400> SEQUENCE: 16
cttcattntt tcttc                                                           15

<210> SEQ ID NO 17
<211> LENGTH: 15
<212> TYPE: DNA
<213> ORGANISM: Simian virus 40
<220> FEATURE:
<221> NAME/KEY: misc_feature
<222> LOCATION: (6)..(6)
<223> OTHER INFORMATION: n is a, c, g, or t

<400> SEQUENCE: 17
cttcantttt tcttc                                                           15
```

FIVE- AND SIX-MEMBERED CONFORMATIONALLY LOCKED 2',4'-CARBOCYCLIC RIBO-THYMIDINES FOR THE TREATMENT OF INFECTIONS AND CANCER

This application is a U.S. National Phase Application under 35 USC 371 of International Application PCT/SE2008/050268 filed Mar. 11, 2008, which claims priority from Swedish Application No. SE 0700649-7 filed Mar. 15, 2007, the entire disclosure of each of which is incorporated herein by reference.

The present invention relates to novel carbocylic analogs of LNA and ENA compounds as disclosed in the description and drawings that follow below, and defined in the appended claims.

In particular the following features are important to the invention:

(1) New 2',4'-carbocyclic fused (5-/6-membered) thymidine (5-carbo-T 12a/12b, in Scheme 1, or 6-carbo-T 23 nucleosides in Scheme 2) are conformationally-constrained nucleosides (North-type). The 5- or 6-carbo-T block(s) has/have been incorporated into antisense oligonucleotides (AON, See Table 3 for example) and their antisense/siRNA properties as gene-directed agent has been evaluated in order to selectively arrest translation of mRNA to protein product.

(2) 5- or 6-carbo-modified AONs have shown high target affinity to complementary RNA strand ($T_m$ increase of +1.5 to +5° C. per modification), depending upon the substitution site in the AON sequence, compared to the native counterpart.

(3) The global helical structure of 5- or 6-carbo-modified AON/RNA hybrids, as revealed by the CD spectra, has been found to be very similar to the native AON/RNA duplex suggesting that the local conformational perturbations brought about by the North-conformationally constrained sugar moiety in 5- or 6-carbo-modifications are not significant enough to be detected by the CD experiment.

(4) All of the 5- or 6-carbo-modified AON/RNA hybrid duplexes have been found to be good substrates for the *E. coli* RNase H1. In these AON/RNA hybrids, a region of 5 to 6 nucleotides in the RNA strand in the 3'-end direction from the site opposite to the 5'- or 6'-carbo-modification site, was found to be insensitive toward RNase H cleavage presumably owing to the local structural perturbations brought about by the conformationally constrained modifications. These cleavage patterns of the 5- or 6-carbo-modified AON/RNA hybrids is uniquely different from that of the oxetane or azetidine modified AONs which had shown found a gap of 5 nucleotides units.

(5) All the 5- or 6-carbo-modified AONs offered greater protection towards 3' exonucleases compared to the native sequence (even more than that of the aza-ENA modifications). In fact, all the modified AONs cleaved at one nucleotide before the modification towards 3'-end and did not degrade any further. These residual AONs have been found to be stable for over 48 h in human serum and with the snake venom phosphodiesterase. This result clearly suggests that a single modification at the second or the third position from the 3'-end can give even more substantial stability towards 3'-exonucleases.

(6) This study provides valuable tools regarding the optimal design of AONs or small interferring RNAs with chimeric RNAs or/and in conjunction with its 2'-modified analogs (siRNA), having completely natural phosphodiester backbone, for the therapeutic applications (down-regulation of an RNA specific to a gene or as a triplexing agent or as an aptamer) that will not only show high target affinity but also high stability towards nucleases in the blood serum.

(7) New 2',4'-linked (5- or 6-carbo)-fused nucleosides in which Nucleobase (N) replaced by 1-Thyminyl [as in Compounds 12a, 12b and 23] or 9-Adeninyl or 9-Guaninyl or 1-Cytosinyl, 5-methyl-1-cytosinyl or 5-trifluoromethyl-1-cytosinyl or 5-fluoro-1-cytosinyl or 5-fluoro-1-cytosinyl or 5-trifluoromethyl-1-Uracilyl moiety (carbo-LNAs and -ENAs) and its derivatives such as mono- di or tri-phosphates and their thio and fluoro analogs can be specifically used to inhibit virus- or -tumor specific proteins, and thereby inactivate the pathogen/tumor growth.

BACKGROUND

Antisense oligonucleotide (AON) can potentially inhibit the protein synthesis by translation arrest/steric blocking or by RNase H mediated degradation of the AON/RNA hybrid. Other methods of gene silencing include formation of triplexes by base-pairing with double-helical DNA (antigene effects), or RNA interference (RNAi), by a short double-stranded RNA (siRNA). The in vivo application of the gene silencing technology warrants chemical modification of the antisense/antigene or siRNA strand to enhance the target affinity, specificity, stability in the blood serum and tissue specific delivery in order to improve overall pharmacokinetic properties. Various modifications of oligonucleotide involving sugar, phosphodiester linkage and nucleobase are known. Of these the phosphorothioate[7] backbone modified oligonucleotides have found some use in therapeutics. Recent years have seen development of conformationally-constrained bicyclic (FIG. 1) and tricyclic nucleotides, in which the sugar is locked in a definite puckered conformation. Such oligonucleotides show promising properties with respect to the target RNA binding and nuclease resistance. Among several molecules reported, short nucleotides containing LNA[1] (≡BNA[2]) modifications have shown unprecedented thermal stability (+3 to +8° C. per modification depending upon the sequence context). The enhanced target binding property of the North-conformationally constrained bicyclic sugar units in these nucleotides has been attributed to the improved stacking between the nearest neighbors and quenching of concerted local backbone motions by LNA nucleotides in ssLNA so as to reduce the entropic penalty in the free energy of stabilization for the duplex formation with RNA. These bicyclic constrained analogs have thus been extensively used to facilitate the down-regulation of genes. The features of LNA/BNA has led to the synthesis of a number of closely related analogs, in which the 2',4'-bridge has been altered[3] or a new type of 1',2'-bridged constraint has been introduced, such as in 1',2'-oxetane[4] or 1',2'-azetidine[5] analog. Such modifications show similar or moderately depressed $T_m$ properties when compared to LNA, but the nuclease resistance or RNase H recruitment properties (for example, ENA,[6] PrNA,[7] and aza-ENA[8]) have turned out to be relatively more favorable than those exhibited by the LNA-containing AONs.

Studies with modified nucleotides show that substituents play important role in conformational steering, controlling hydration, inducing hydrophobic/hydrophilic interactions, and generally using the electrostatic interactions to neutralize, for example, the phosphates charge, as well as to influence interaction of modified oligonucleotide with other nucleotides and/or enzymes present in the system. We and others have argued that replacement of the hydrophilic 2'-oxygen of LNA or ENA or 2'-nitrogen from their amino analogs by the hydrophobic carbocyclic analogs would steer both target affinity as well as the nuclease stability in the blood serum because of change in the immediate shell of hydration. Recently,[14] the ring-closing metathesis approach had been employed to synthesize two carbocyclic analogs of ENA with three carbons locking the C2' and C4' (compounds K/L in FIG. 1). These carbocyclic analogs had been incorporated into AONs with natural phosphodiester backbone which lead to increased thermal stability ($T_m$) by 2.5-4.5° C./modification with the complementary RNA. However, no blood serum or 3'-exonuclease stability or the RNase H recruitment capability of these carbocyclic analogs has so far been reported.

SUMMARY OF THE INVENTION

The invention provides a novel synthetic strategy for the carbocyclic analogs of LNA[12] and ENA[13] thymidines (carbocyclic-LNA-T and carbocyclic-ENA-T), which have been accomplished using intramolecular free-radical ring closure reaction between a radical generated at C2' and strategically placed double bond in the modified pentofuranose moiety of nucleoside. We have subsequently incorporated carbocyclic-LNA-T [$T_{(5-carbo)}$] and carbocyclic-ENA-T [with $T_{(6-carbo)}$] in to the AONs and studied their blood serum stabilities, as well as their RNase H recruitment capabilities and compared these properties with isosequencial LNA and aza-ENA containing counterparts.

In particular the invention provides novel compounds as defined in claim 1. In a further aspect the invention provides medicaments comprising compounds according to the invention. In particular these medicaments can be used for the treatment of cancer.

The compounds can also be used for diagnostic and analytical purposes for identification of viral or bacteria specific DNA or RNA.

The invention will be further illustrated below with reference to the drawings, in which FIG. 1. shows structures of various bicyclic North-type conformationally-constrained α/β-D/L-pentofuranosyl nucleosides: (A) LNA[1]; (B) amino-LNA[3]; (C) xylo-LNA[9]; (D) α-L-LNA[10]; (E) β-bicyclonucleoside[11]; (F) 1',2'-oxetane-bridged[4]; (G) azetidine-bridged[5]; (H) ENA[7,11-13], (I) aza-ENA[8] (J) PrNA[7]; (K) unsaturated carbocyclic analog of LNA[27 14]; (L) saturated carbocyclic analog of LNA.[14]

Figure 2:
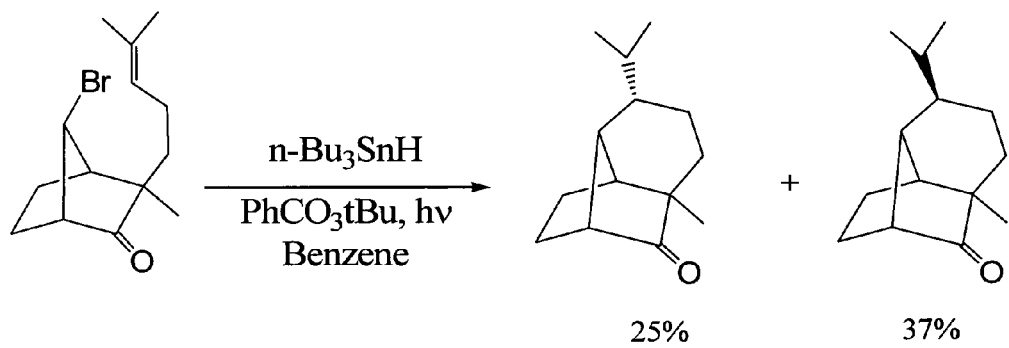

FIG. 2. shows Heptenyl cyclization of 7-norborneyl radical.[15]

Figure 3:
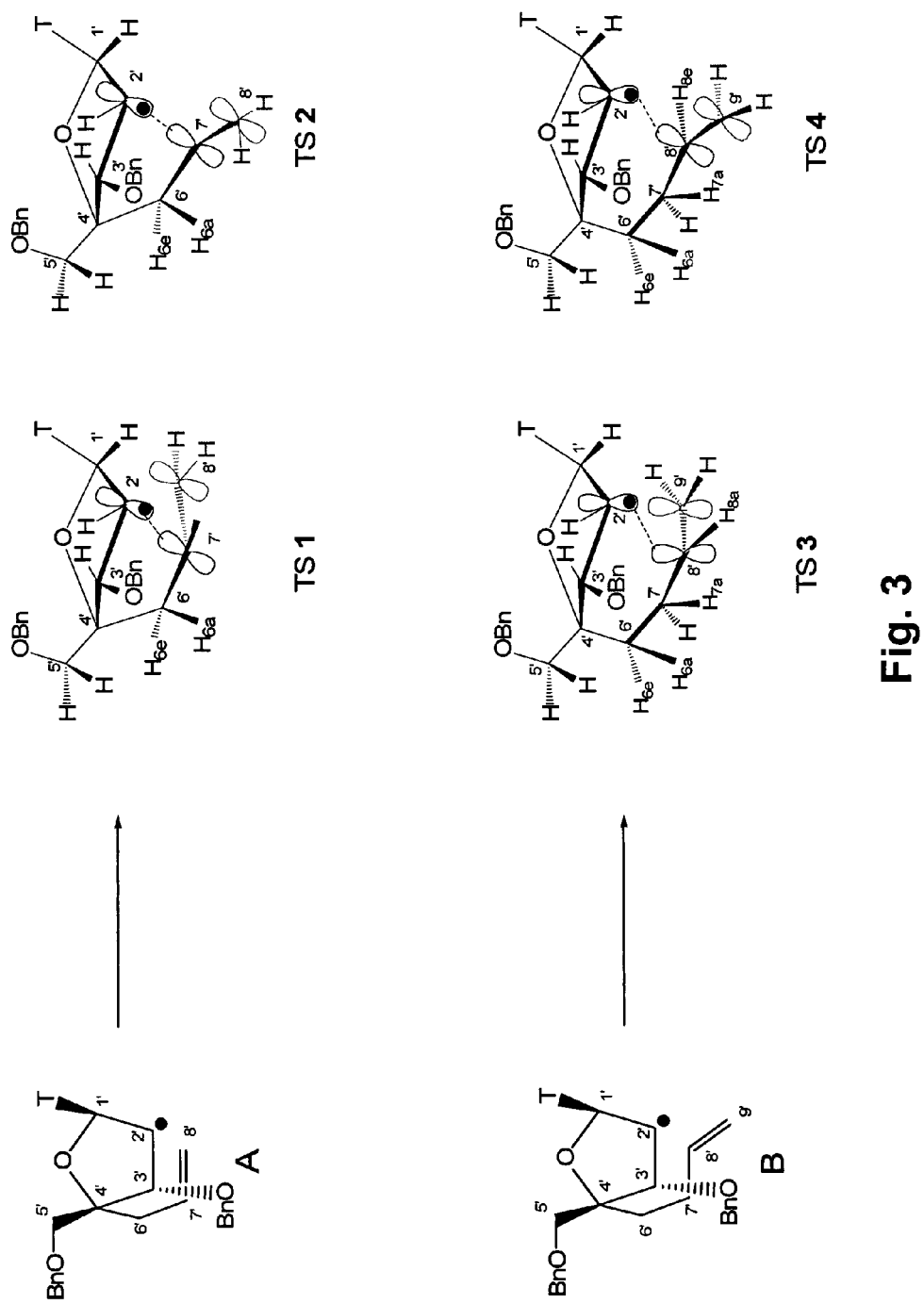

FIG. 3. (A): 5-exo-cyclization through two transition states TS 1 and TS 2 leading to favored 5-membered carbocyclic 2',4'-cis fused bicyclic system with R-configuration of C7' chiral center as well as to the counterpart with the disfavored S configuration of C7'. (B): 6-exo-heptenyl cyclization through two transition states TS 3 and TS 4 leading to favored carbocyclic 2',4'-cis fused bicyclic system with R-configuration of C8' and its counterpart with C8' chiral center in the disfavored S configuration.

Figure 4A:
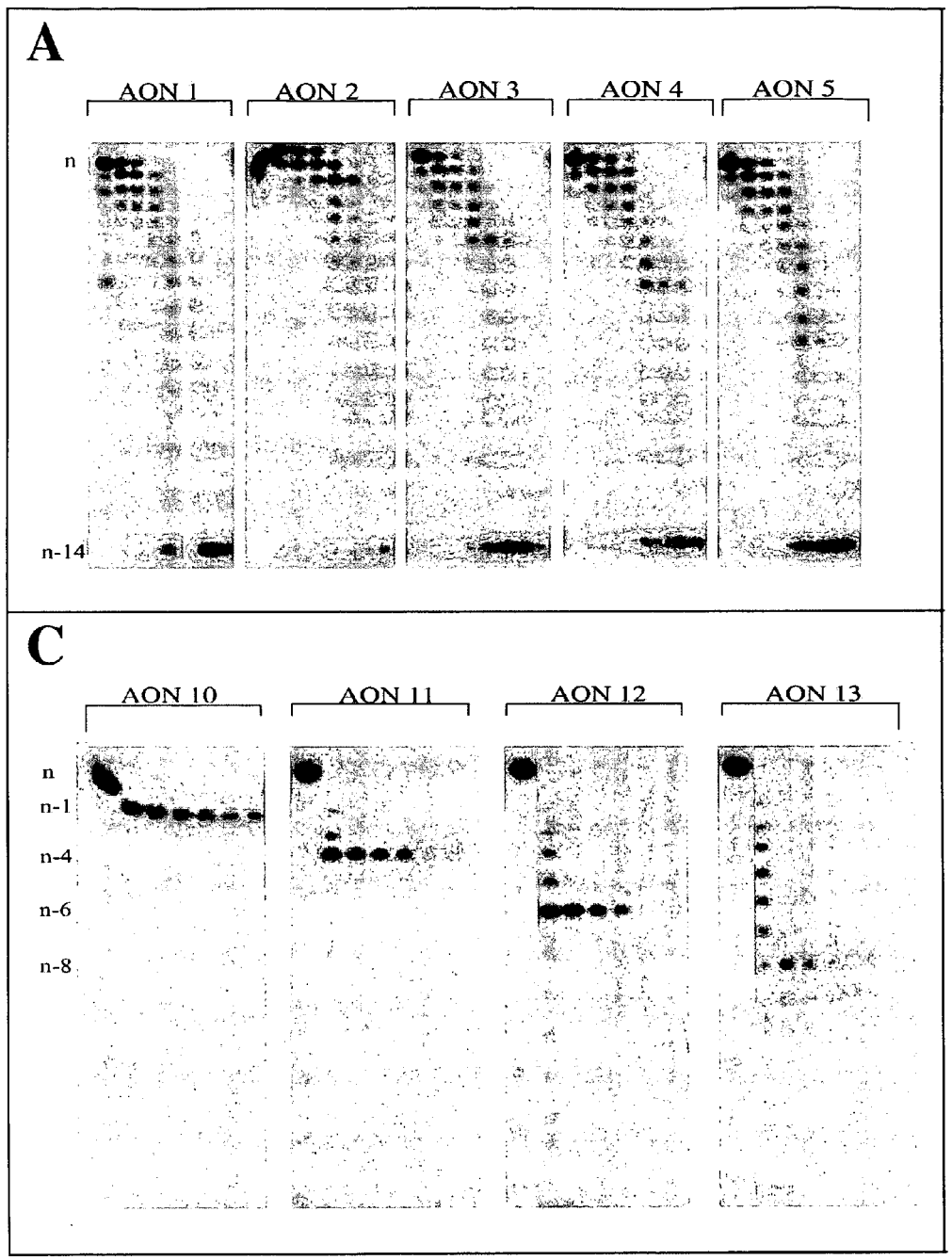
Figure 4B:
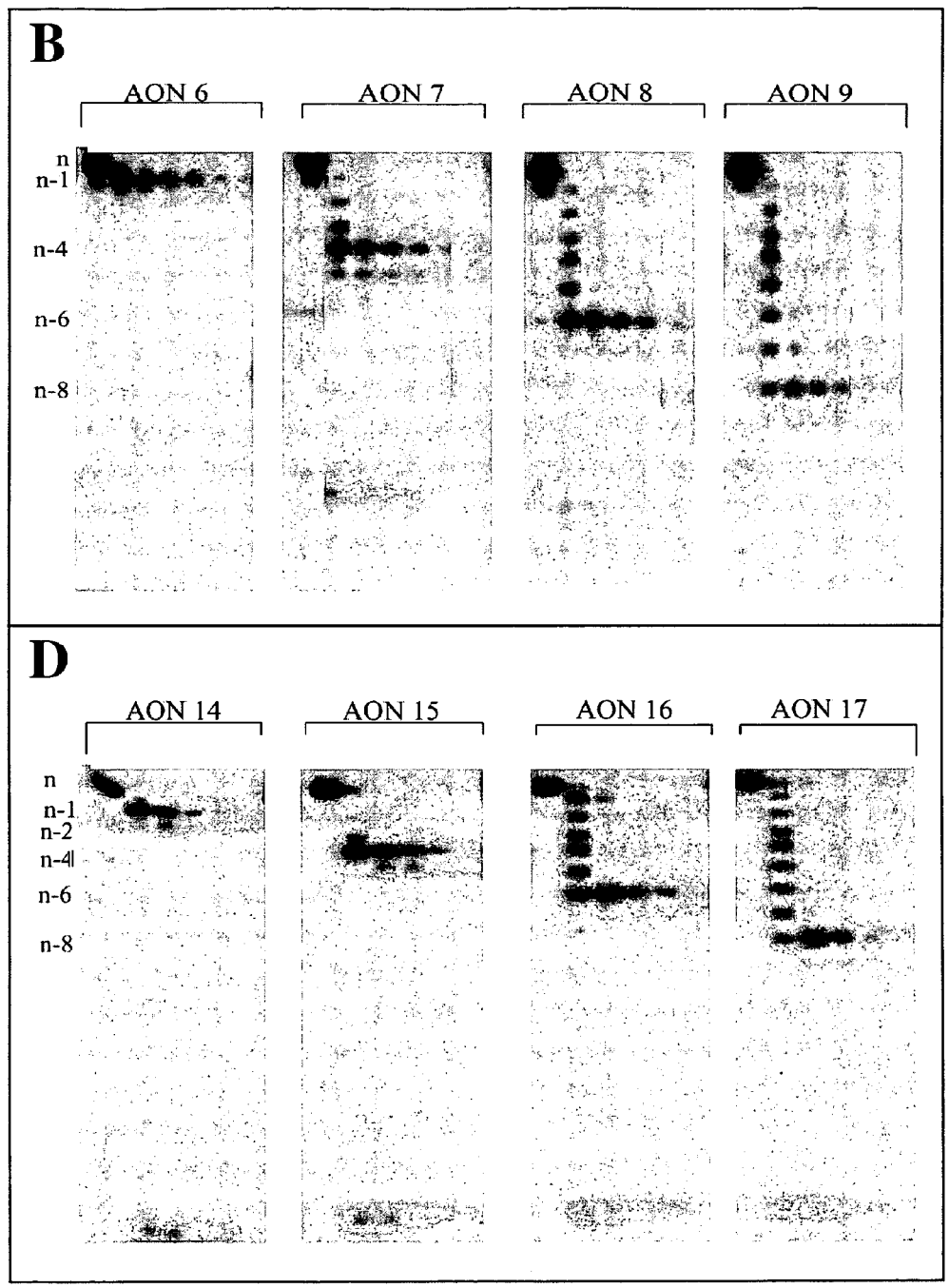

FIG. 4. Autoradiograms of 20% denaturing PAGE showing degradation patterns of 5'-$^{32}$P-labeled AONs in human blood serum (Table 1 for all AON sequences). Inset A: AON 1 and LNA-modified AONs 2-5. Inset B: Carbocyclic-LNA-modified AONs 6-9. Inset C: Carbocyclic-ENA-modified AONs 10-13 and Inset D: aza-ENA-modified AONs 14-17. Time points are taken after 0, ½, 1 h, 2 h, 5 h, 7 h, 9 h, 12 h, for AONs 1-5 and 0 h, 6 h, 8 h, 12 h, 24 h, 36 h and 48 h of incubation for AONs 6-17 at 21° C. (see Experimental Section for details).

Figure 5:
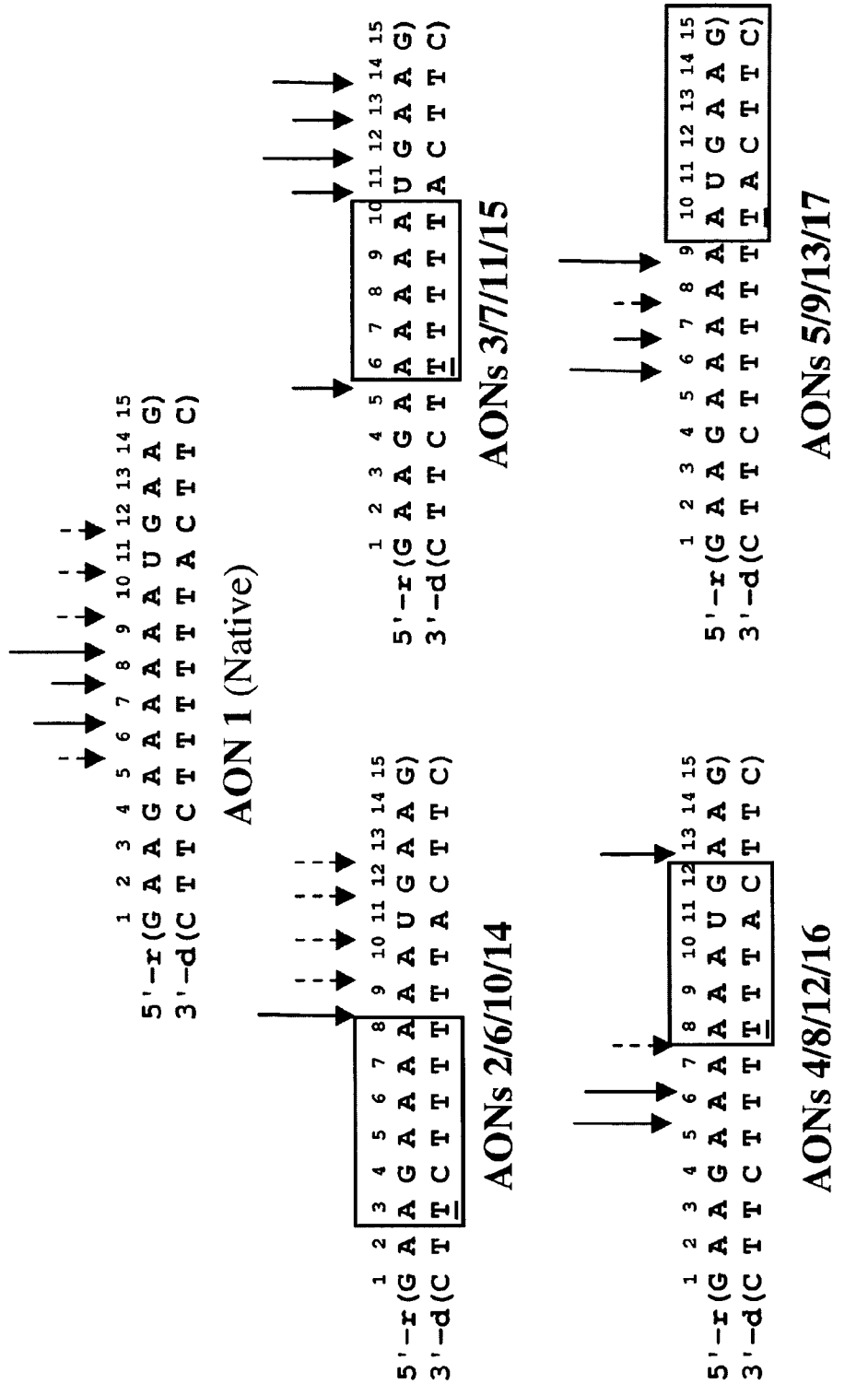

FIG. 5. The RNase H1 cleavage pattern of AONs 1-17/RNA heteroduplexes. Vertical arrows show the RNase H cleavage sites, with the relative length of the arrow showing the extent of the cleavage. The square boxes around a specific sequence shows the stretch of the RNA, which is resistant to RNase H cleavage thereby giving footprints (see PAGE autoradiograms in FIG. 6).

Figure 6A:
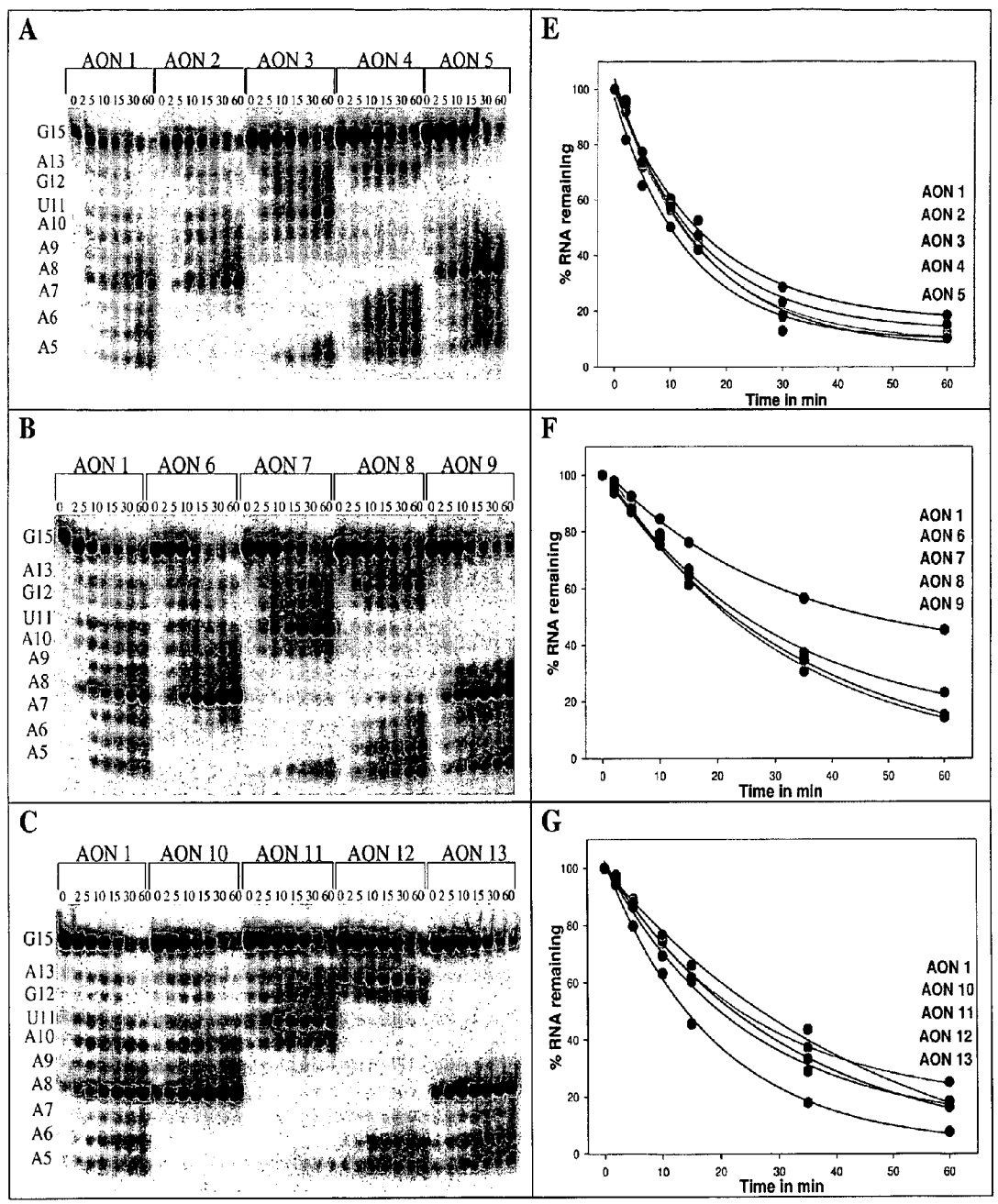
Figure 6B:
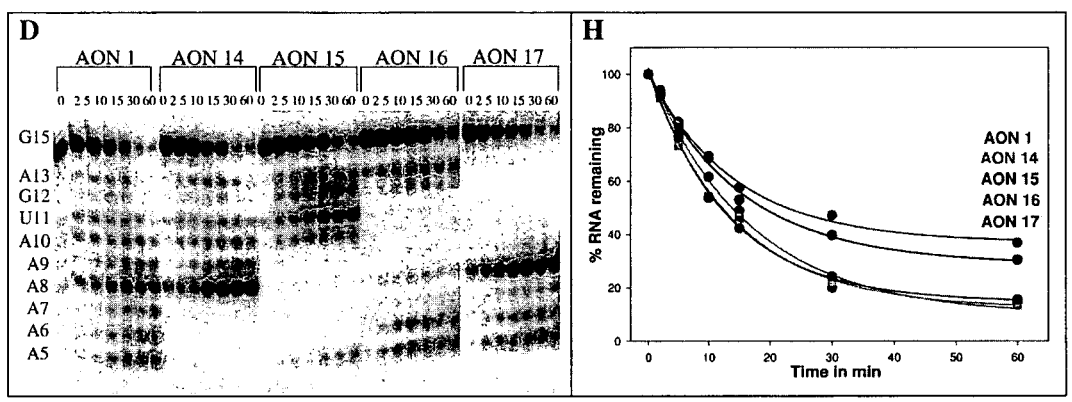

FIG. 6. Autoradiograms of 20% denaturing PAGE, showing the cleavage kinetics of 5'-$^{32}$P-labeled target RNA by *E. coli* RNase H1 in the AONs 1-17 after 2, 5, 10, 15, 30 and 60 min of incubation. Conditions of cleavage reactions: RNA (0.8 μM) and AONs (4 μM) in buffer containing 20 nM Tris-HCL (pH 8.0), 20 mM KCL, 10 mM Mgcl2, and 0.1 mM DTT at 21° C.; 0.04 U of RNase H1. Inset A: LNA-T modified AONs 2-5 with native AON 1. Inset B: carbocyclic-LNA-T modified AONs 6-9. Inset C: carbocyclic-ENA-T modified AONs 10-13 with native AON 1. Inset D: aza-ENA-T modified AONs 14-17 with native AON 1. The graphs in Insets E, F, G, and H show the kinetics of RNase H1 mediated cleavage of the target RNA, the remaining fraction of target RNA is measured densitometrically and plotted as a function of time fitted to a single exponential decay function. Inset E: AON 1 with AONs 2-5. Inset F: for AON 1 with AONs 6-9. Inset G: AON 1 and AONs 10-13. Inset H: AON 1 and AONs 14-17.

Figure 7:
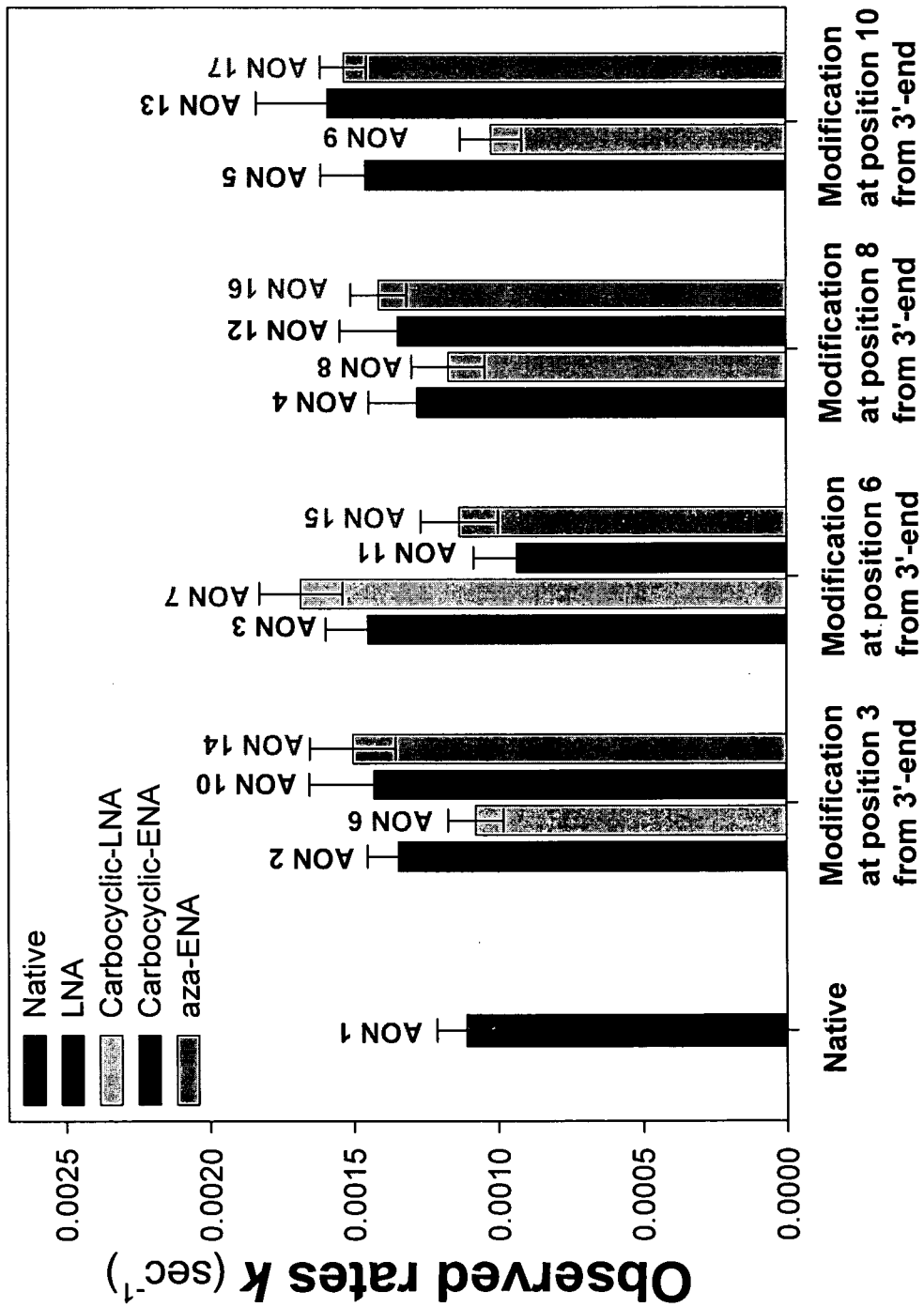

FIG. 7. Bar plots of the observed cleavage rates of the RNase H promoted degradation of AONs 2-17/RNA heteroduplexes with various modifications (LNA-T, carbocyclic-LNA-T, carbocyclic-ENA-T and aza-ENA-T) in the AON strand at position 3, 6, 8 and 10 from the 3'-end, in comparison to that of the native counterpart AON 1. The observed initial cleavage rates ($sec^{-1}$) of AONs 1-17/RNA heteroduplexes by *E coli* RNase H are found to be very similar, while in the human blood serum (FIGS. 8-11) the degree of stability varied widely for the carbocyclic versus heterocyclic modified AONs reflecting their respective hydrophobic/hydrophilic properties.

Figure 8:
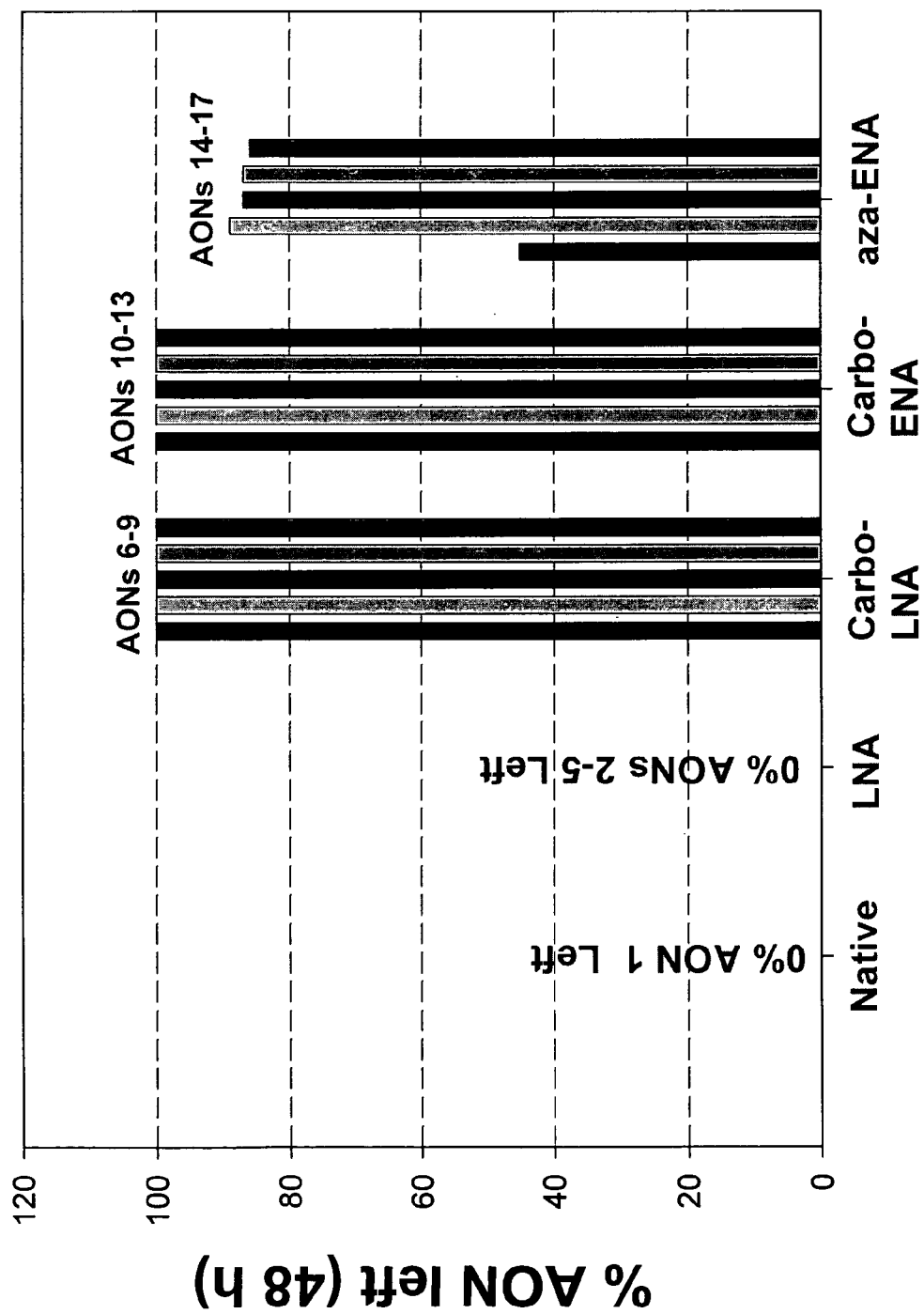

FIG. 8. The percent of AONs 6-17 left after 48 h of incubation in the human blood serum at 21° C. Note that, under similar condition, the native (AON 1) and LNA-containing AONs (AONs 2-5) were fully degraded after 12 h, and shown in blank (red colored). Note that the human blood serum stable product, (i) is (n−1) for the AONs 6/10/14 (AONs substituted at position 3 from 3'-end) after the hydrolysis of 3'-terminal nucleotide, (ii) (n−4) product for the AON 7/11/15 (AONs substituted at position 6 from the 3'-end), (iii) the (n−6) product for the AONs 8/12/16 (AONs substituted at position 8 from 3'-end), whereas (iv) the (n−8) product was formed from AONs 9/13/17 (AONs substituted at position 10 from 3'-end). Thus the concentration of these final hydrolysis products formed as a result of introduction of a specific modification at a particular site was taken as 100%. Also note: cleavage of one nucleotide from the 3'-end is (n−1), and the cleavage of two nucleotides from the 3'-end is (n−2), and so on, where 'n' is the full length AON.

RESULTS AND DISCUSSION

The intramolecular radical addition reactions to the tethered double-bond involving both 5-hexenyl and 6-heptenyl radicals have been well studied by Beckwith, Baldwin, Giese, Curran, Stork, and more recently by Rajanbabu. The efficiency and regiochemistry of such intramolecular cyclization addition reactions have been shown to be controlled by (i) the initial radical structure (ii) the steric effects resulting from the olefin substitution pattern, and (iii) the geometric constraints on the chain linking the radical centre, and the tethered double bond.

In the kinetically controlled rearrangement of variously substituted 5-hexenyl radicals, the preference for the exo versus endo mode, i.e the formation of the 5-membered over the 6-membered ring, is well understood in terms of relatively strain-free chair-like transition state accommodating the stereoelectronic requirements of radical addition to the double bond. The model also provides satisfactory explanation for the observed stereoselectivities in the cyclization of 2-, 3- and 4-substituted hexenyl radicals (5-hexenyl nomenclature) on account of the preferred adoption of pseudo-equatorial positions by the substituents in the respective transition states.

It is known that the ring-closure reaction involving cyclic 5-hexenyl radicals (i.e., radical as a part of the cyclic ring) is similar to that of the open-chain systems except that the ring imposes steric constraints on the stereochemical outcome of the reaction. The initial radical forms the most stable structure with bulky substituents in equatorial/pseudo-equatorial position, when the radical centre is a part of the sugar ring. Ring-closure reaction occurs via attack of a radical centre oriented to pseudo-equatorial position on the axially substituted alkenyl chain resulting in the cis-fused rings. It is also known that the alkenyl chain preferentially occupies an axial position, since an equatorial alkenyl chain results in poor overlap of the semi-occupied molecular orbitals and π* orbitals.

The substituents play their role on account of their steric bulk or stereoelectronic nature as they interact with the ring atoms/substituents at different positions of alkenyl chain during intramolecular 5-hexenyl cyclization. For example, it has been shown that substituents on C1 and C4 atoms (5-hexenyl nomenclature) of the initial radical are the major factors dictating stereochemistry of the newly formed 1,5-bond. Thus when both C1 and C4 substituents are present predominantly a 1,5-cis isomer is formed. With no substitution at C4 (i.e. C4-deoxy), a mixture of 1,5-cis and 1,5-trans fused products is formed. In the presence of vinylic oxygen the boat-like transition state is stabilized resulting in formation of 1,5-trans isomer.

In contradistinction, the formation of 6-membered rings by free radical reactions involving 6-exo cyclizations of heptenyl system presents at least two problems: first, the rate constant of 6-hepetenyl cyclization is ≈40 times slower than the corresponding 5-hexenyl cyclization, thus the competing radical quenching by reduction with nBu₃SnH becomes a serious problem; second, the endo mode of cyclization is only ≈7 times less rapid than the exo mode of cyclization, thus formation of the endo products also competes with the 6-membered products. Thus far, most of the fused bicyclic ring formation reactions studied have been of 1,2-type, i.e. the radical center is located at the neighboring carbon to the tethered double bond.

Here we present two unusual reactions involving the 5-hexenyl or the 6-heptenyl radical cyclization by forming C—C bond from a distant double bond at C4' toward C2' radical center of the ribofuranose ring of thymidine (Scheme 1). The 2',4'-free-radical cyclization is a key step in our synthetic strategy to efficiently yield North-type conformationally constrained cis-fused bicyclic 5-membered and 6-membered carbocyclic analogs of LNA (carbocyclic-LNA-T) and ENA (carbocyclic-ENA-T), as it has been originally used in the construction of conformationally constrained nucleosides by Wengel's and Imanishi's group in the ionic ring-closure reaction. To the best of our knowledge the only other similar case of radical cyclization reported had been involving tethered double bond (butenyl side chain) and a cyclic radical (FIG. 2) in the constrained norbornyl system.[50] The double-bond chain and the free-radical in the norbornyl system were positioned at C1 and C3 to each other with the stereochemistry being dictated by topological and steric constraints with four asymmetric centers, giving the 1,6-cis fused (37%) and 1,6-trans-fused (25%) cyclohexyl ring through the participation of presumably chair-like 6-heptenyl cyclization. Clearly, in our case (FIG. 3) the site of the propenyl or the butenyl substituent at C4' with respect to the radical centre at C2' in the flexible 5-membered pentofuranose ring led us to assume that our free-radical cyclization reaction may have poorer steric and stereoelectronic control on the formation of chair-like or/and boat-like transition state to give the 1,3-cis fused ring closure product(s).

Scheme 1:

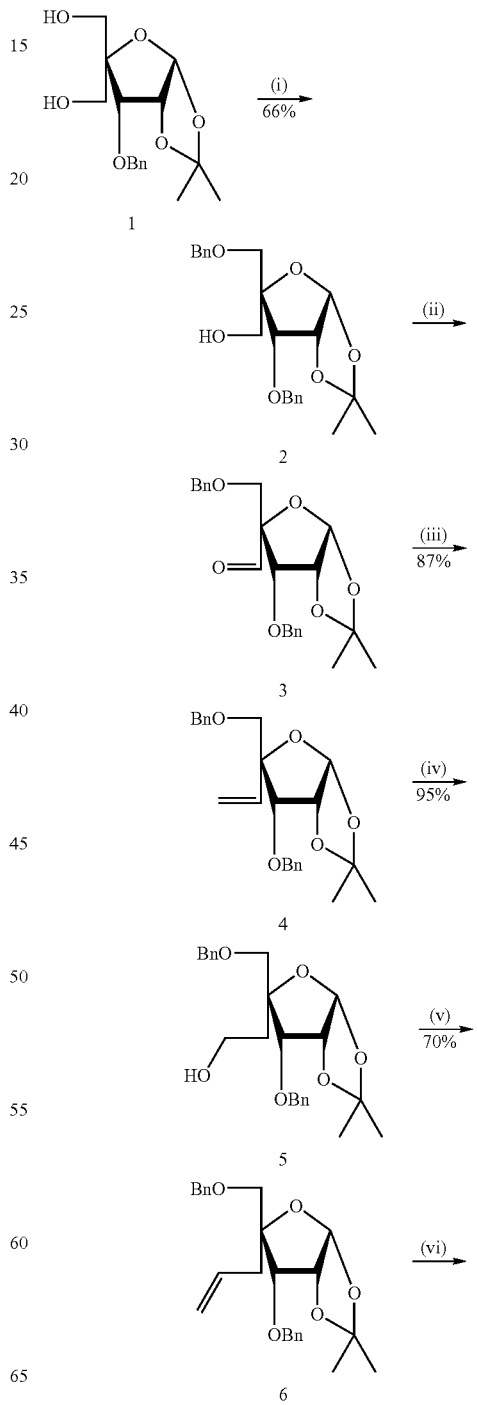

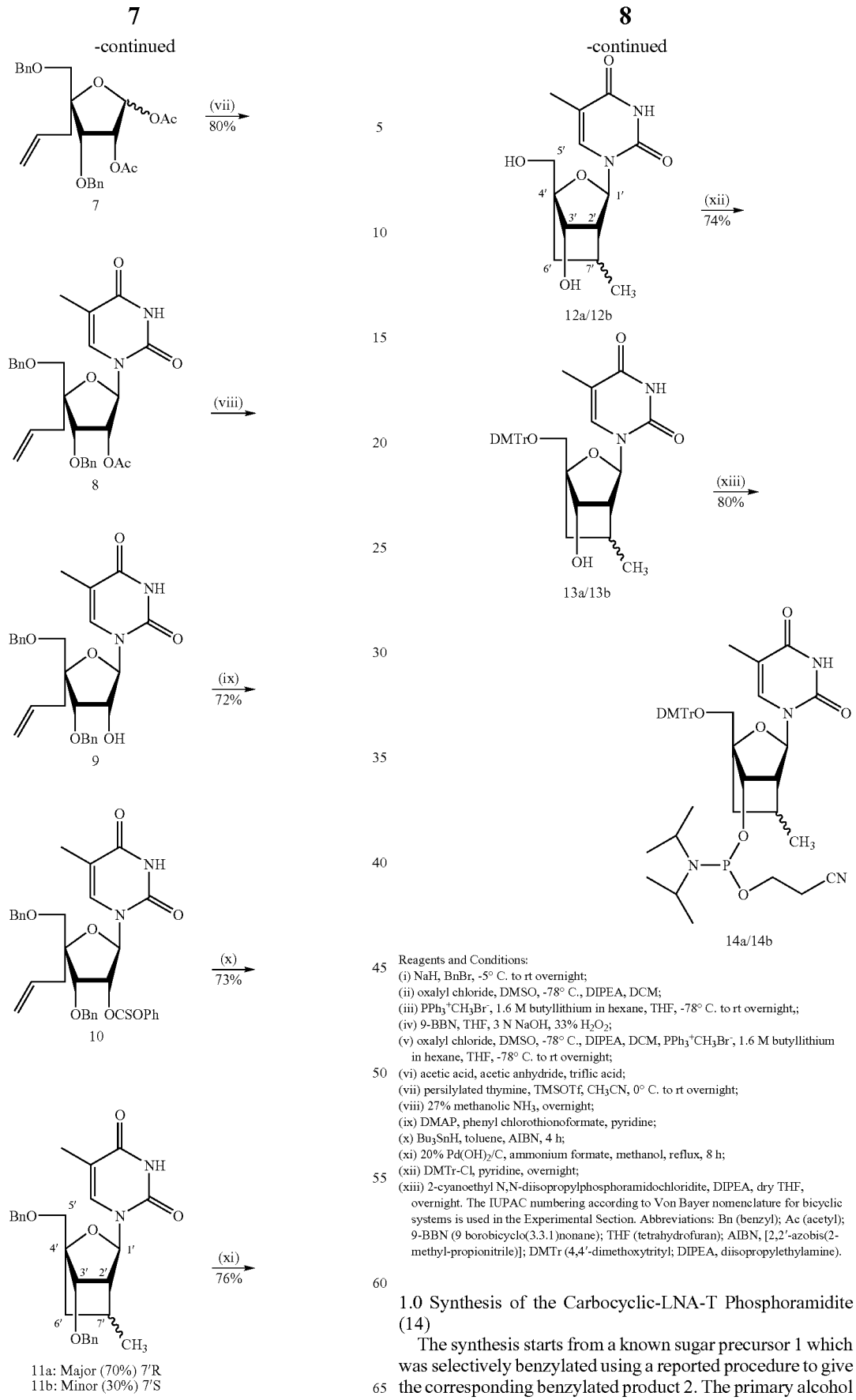

Reagents and Conditions:
(i) NaH, BnBr, -5° C. to rt overnight;
(ii) oxalyl chloride, DMSO, -78° C., DIPEA, DCM;
(iii) PPh$_3^+$CH$_3$Br$^-$, 1.6 M butyllithium in hexane, THF, -78° C. to rt overnight,;
(iv) 9-BBN, THF, 3 N NaOH, 33% H$_2$O$_2$;
(v) oxalyl chloride, DMSO, -78° C., DIPEA, DCM, PPh$_3^+$CH$_3$Br$^-$, 1.6 M butyllithium in hexane, THF, -78° C. to rt overnight;
(vi) acetic acid, acetic anhydride, triflic acid;
(vii) persilylated thymine, TMSOTf, CH$_3$CN, 0° C. to rt overnight;
(viii) 27% methanolic NH$_3$, overnight;
(ix) DMAP, phenyl chlorothionoformate, pyridine;
(x) Bu$_3$SnH, toluene, AIBN, 4 h;
(xi) 20% Pd(OH)$_2$/C, ammonium formate, methanol, reflux, 8 h;
(xii) DMTr-Cl, pyridine, overnight;
(xiii) 2-cyanoethyl N,N-diisopropylphosphoramidochloridite, DIPEA, dry THF, overnight. The IUPAC numbering according to Von Bayer nomenclature for bicyclic systems is used in the Experimental Section. Abbreviations: Bn (benzyl); Ac (acetyl); 9-BBN (9 borobicyclo(3.3.1)nonane); THF (tetrahydrofuran); AIBN, [2,2'-azobis(2-methyl-propionitrile)]; DMTr (4,4'-dimethoxytrityl; DIPEA, diisopropylethylamine).

1.0 Synthesis of the Carbocyclic-LNA-T Phosphoramidite (14)

The synthesis starts from a known sugar precursor 1 which was selectively benzylated using a reported procedure to give the corresponding benzylated product 2. The primary alcohol in sugar 2 was oxidized to the corresponding aldehyde 3 employing Swern oxidation. The vinyl chain at C4 was then introduced by the Wittig reaction[61] on the crude aldehyde 3 to give the vinyl sugar 4 (87% in two steps from 2). The olefin 4 was converted to C4-hydroxyethyl derivative via successive hydroboration-oxidation using 9-BBN/NaOH—$H_2O_2$ to give 5 in 95% yield, which was again subjected to Swern oxidation/Wittig reaction to give the required C4-allylated sugar 6 (70% in two steps from 5) with strategically placed propenyl side chain at C4 for 5-hexenyl type free radical cyclization. Compound 6 was subjected to acetolysis using a mixture of acetic anhydride, acetic acid and triflic acid to give the corresponding diacetate 7 quantitatively as α/β anomeric mixture (single spot on TLC and proven by $^1$H-NMR) using. The crude diacetate 7, after bicarbonate workup, was subjected to modified Vorbruggen reaction involving in situ silylation of thymine and subsequent trimethylsilyl triflate mediated coupling to give thymine nucleoside 8 in 80% yield in two steps from 6. The β configuration of the product 6 was confirmed by 1D differential NOE experiment, which showed 3% enhancement of H2', and 1% enhancement of H3' upon irradiation of H6 ($d_{H6-2'}$≈2.3 Å for β anomer). Deacetylation of compound 8 using 27% methanolic ammonia overnight, and subsequent esterification using phenylchlorothioformate yielded the desired precursor 10 for radical cyclization. The key free radical cyclization reaction was carried out using $Bu_3SnH$ with radical initiator AIBN at 115° C. in degassed ($N_2$) toluene. To ensure that the radical generated has adequate lifetime to capture the double bond before it is quenched by hydrogen radical, the concentrations of $Bu_3SnH$ and AIBN were maintained through high dilution and slow drop-wise addition. The 5-hexenyl type exo mode cyclization of the radical to C4'-propenyl double-bond yielded exclusively the expected[34] 5-membered 2',4'-cis-fused carbocyclic product with bicyclo[2.2.1]heptane skeleton as inseparable diastereomeric mixture of compound 11a (major compound 70%, 7'R) and 11b (minor compound 30%, 7'S).

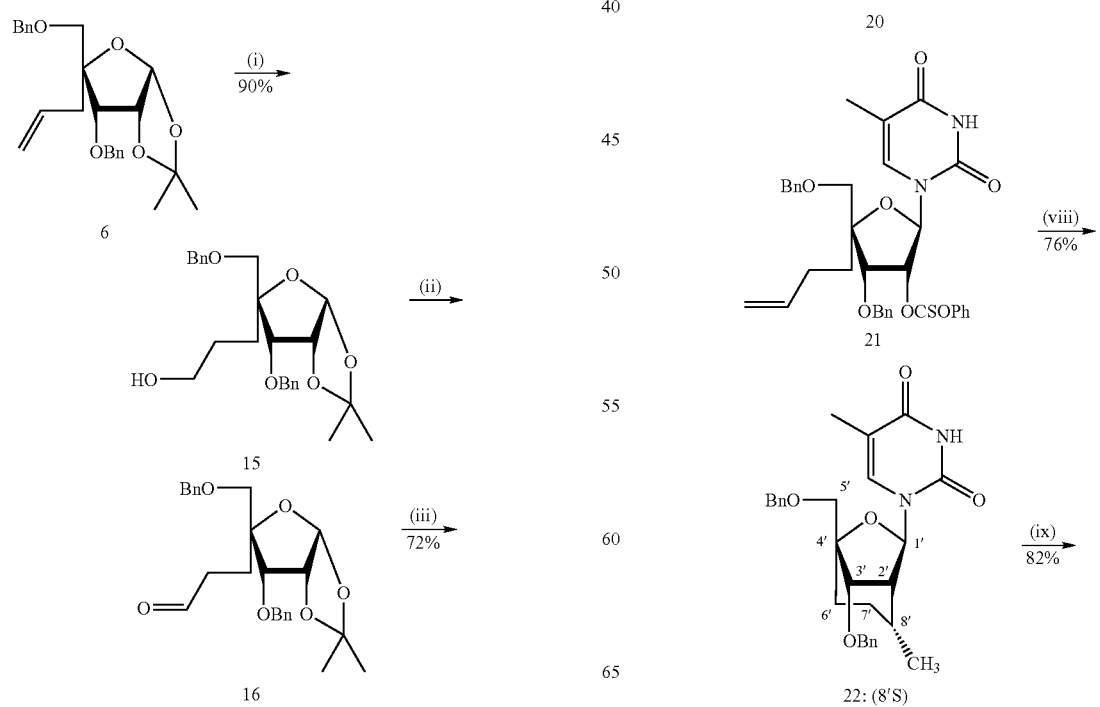

Scheme 2:

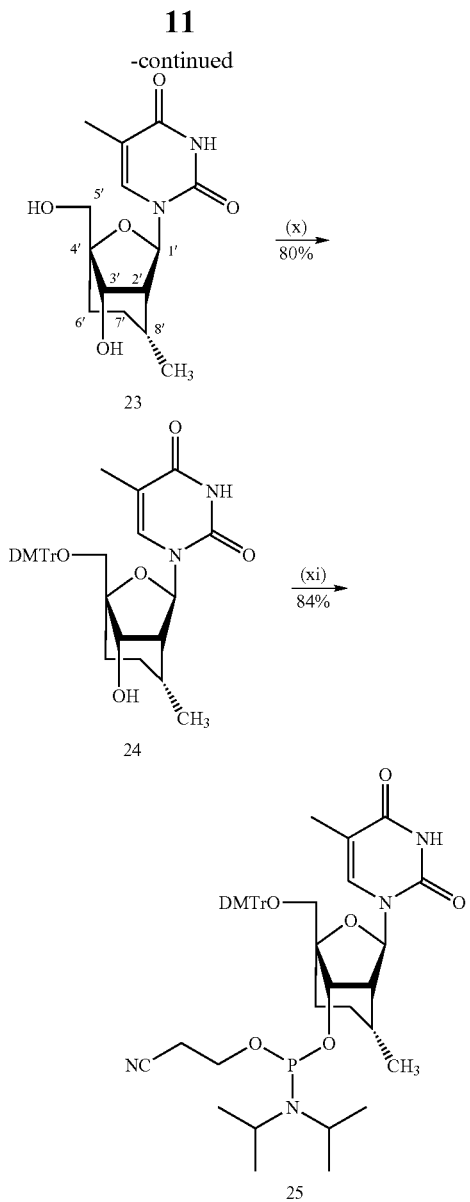

Reagents and Conditions:
(i) 9-BBN, THF, overnight, 3 M NaOH, 33% H$_2$O$_2$;
(ii) oxalyl chloride, DMSO, -78° C., DIPEA, CH$_2$Cl$_2$;
(iii) PPh$_3^+$CH$_3$Br$^-$, THF, 1.6 M butyllithium in hexane, -78° C. to rt overnight;
(iv) acetic acid, acetic anhydride, triflic acid;
(v) persilylated thymine, TMSOTf, CH$_3$CN, 0° C. to rt overnight;
(vi) 27% methanolic NH$_3$, overnight;
(vii) DMAP, phenyl chlorothionoformate, pyridine, rt overnight;
(viii) Bu$_3$SnH, toluene, AIBN, 4h, reflux;
(ix) 20% Pd(OH), ammonium formate, methanol, reflux, 12h;
(x) DMTr-Cl, pyridine, rt overnight;
(xi) 2-cynoethyl N,N-diisopropylphosphoramidochloridite, DIPEA, dry THF. The IUPAC numbering according to Von Bayer nomenclature for bicyclic systems is used in the Experimental Section. Abbreviations: Bn (benzyl); Ac (acetyl); 9-BBN (9 borobicyclo(3.3.1)nonane); THF (tetrahydrofuran); AIBN, [2,2'-azobis(2-methyl-propionitrile)]; DMTr (4,4'-dimethoxytrityl); DIPEA (diisopropylethylamine).

The formation of the bicyclic nucleosides 11a and 11b, with a North fused conformationally constrained pentofuranosyl moiety was confirmed by long range $^1$H-$^{13}$C NMR correlation (HMBC)[63] and $^1$H—$^1$H (TOCSY) for both the isomers (see Section 4). 1D differential NOE experiment (FIG. 5) established that the exocyclic methyl at C7' is in close proximity to H1' in the major isomer (d$_{7'-Me/H1'}$=2.8 Å for R and 4.4 Å for S configuration at C7') of the bicyclic structure. The benzyl groups in the bicyclic nucleosides 11a/11b were de-protected using Pd(OH)$_2$/C and ammonium formate in methanol to give the corresponding dihydroxy compounds 12a and 12b respectively (see Section 4). Several attempts to separate this diastereomeric mixture of 12a/12b failed in our hands. We therefore subjected it directly to 5'-dimethoxytritylation (74%) to give 13 followed by 3'-phosphitylation (80%) to give the phosphoramidite 14 using standard conditions.

2.0 Synthesis of Carbocyclic-ENA-T Phosphoramidite (25)

For the synthesis of carbocyclic-ENA-T analog heptenyl type of free-radical intermediate was warranted, and thus the C4-allylated sugar 6 obtained in the previous scheme was subjected to another round of hydroboration-oxidation followed by Swern oxidation and Wittig reaction as for 4, 5 and 6 as in Scheme 1 yielded 15 (90%), 16 and 17 (72% in two steps) respectively. The sugar 17, was subjected to acetolysis followed by modified Vorbruggen-type coupling as for compound 7 and 8 in Scheme 1 gave 18 and β-configured thymine nucleoside 19 in 70% yield in two steps. Deacetylation with 27% methanolic ammonia followed by esterification using phenylchlorothioformate yielded the ester 21 (60% yield). Purified ester was then subjected to free radical cyclization utilizing tributyltin hydride in presence of radical initiator AIBN. Though for heptenyl type of cyclization the endo mode is only 7 times less rapid than exo mode cyclization in addition to the competing 1,5-hydrogen abstraction[48] however, gave exclusively exo-product 22 in modest 76% yield. The bicyclic nucleoside 22 was de-protected using Pd (OH)$_2$/C and ammonium formate in methanol to give the corresponding
dihydroxy compound 23 with 6-oxa-bicyclo[3.2.1]octane in 82% yield. Dimethoxytritylation (80%) followed by phosphitylation using standard conditions gave the fully protected phosphoramidite 25 in 84% yield.

3.0 Mechanism of the Ring-Closure Reaction

Two possible transition states TS 1 and TS 2 could be involved in the radical cyclization of the C4'-propenyl system through 5-exo-hexenyl intermediate (structure A in FIG. 3) in which case these transition states should represent the low-energy chair forms with newly developing C7' methyl substituent in the pseudo-equatorial (TS 1) or pseudo-axial (TS 2) orientation. Although both transition states are probable, the experimental evidence (7:3 proportion of major to minor products) suggests that the absence of 1,3-diaxial interactions of methyl group at C7' (C7' in R configuration) with bulky protective Bn-group at the pseudo-axial O3' (11a) is energetically more favorable and the product with methyl group at C7' in S-configuration (11b) is the minor product. We anticipate that the energy of stabilization of the transition state TS 1 is slightly more because of the absence of any non-bonding/steric interaction compared to that in the TS 2.

Similar considerations can be used to understand the mechanism of the 6-exo-heptenyl cyclization of substituted nucleoside radical B (FIG. 3). For cyclization to occur, two favorable (out of four possible) configurations obtained by rotation around C6'-C7' in the side chain, C4'-C6'-C7'-C8', and around C7'-C8' in the C6'-C7'-C8'-C9' represent probable transition states TS 3 and TS 4. The position of C7'-C8' double bound is apparently in a close proximity of the forming radical at C2' which makes the cyclic product arising from the TS 3 transition state (FIG. 3) a preferable reaction path. The newly developing C8' methyl substituent thus takes up the equatorial position, in which the 1,3-diaxial interaction with the C3' axial substituent (OBn) in the newly formed fused cyclohexyl ring is absent, which makes it more favored then the product with chiral C8' in S-configuration.

The orientation of the transition state, TS 4 in FIG. 3, on the other hand, is also in a chair conformation, with site of attack in the double-bond (C8') and the radical centre at C3' in the steric proximity in order to ensure 6-exo-heptenyl cyclization with minimal entropic penalty. This orientation in TS 4, however, exhibits two 1,3-diaxial interactions, one between the 3'-O-benzyl substituent and the newly developing axial methyl substituent at C8' and, second, between the newly forming C8' methyl substituent and the axial proton at C6'. The presence of two 1,3-diaxial interactions would result in a energetically disfavored transition state, as shown in TS 4, compared to that in TS 3, which explains why we observe the exclusive formation of the cyclic product with equatorial methyl at C8' (FIG. 3).

4.0 Assignment of $^1$H and $^{13}$C Chemical Shifts and Evidence for the Ring Closure in the Five-Membered Fused Carbocyclic-LNA-T (12a & 12b) and the Six-Membered Carbocyclic-ENA-T (23).

The $^1$H spectrum at 600 MHz of the ring-closure reaction of the parent olefin 10 revealed that the product formed is an intractable diastereomeric mixture of the sugar-fused 5-membered bicyclic 3',5'-di-O-benzyl protected nucleosides 11a/11b (Scheme 1). However, because of the overlap of the H7' and H2' peaks in 11a/11b, firm NMR evidence could not be obtained for the carbon-carbon ring closure between C2' and C7'. It is noteworthy that the high resolution mass spectrometry would not be able to discriminate between the mass of 2'-deoxy counterpart of 10 (formed as a result of 2'-deoxygenation and subsequent quenching by a hydrogen radical) and the cyclized product 11a/11b. The H7' and H2' peaks in the de-protected compounds 12a/12b were however fully resolved, and hence could be successfully used for full NMR characterization.

The $^1$H spectrum (FIG. S22 in SI), showed the presence of two diastereomers, a major (12a) as well as a minor isomer (12b) in ca. 7:3 ratio. The upfield H2' at δ2.43 along with H7' at δ2.65 and their proton-proton couplings, proven by detailed double decoupling (FIGS. S24 and S26 in SI) and by COSY experiments (FIGS. S30-S32 in SI), shows that the C2' substituent is the C7' methine-carbon. The nOe enhancement (~12%, corresponds to ca. 2.6 Å) between H6 (thymine) and H3' (FIGS. S35 and S36 in SI), of 12a/12b, in addition to $^3J_{H1',H2'}$=0 Hz, further confirms that the sugar is indeed locked by the fused carbocycle in the North conformation as observed for other North-locked nucleosides such as ENA[13], LNA[12], and aza-ENA. This further shows that the 1-thyminyl moiety is in p-configuration and anti-conformation across the glycoside bond. The fact that the nOe enhancement of 6.5% for H1' upon irradiation on CH$_3$ at CT of 12a (FIG. S35 in SI) is found, shows that the methyl group on C7' is in close proximity of H1' (ca. 2.8 Å), thereby confirming the R configuration for C7'. The nOe enhancement of 4.5% for H7' in 12b (FIG. S36 in SI) upon irradiation on H1', on the other hand, confirms that the H7' is in close proximity of H1' (ca. 2.2 Å) and hence the S configuration is assigned for C7'. $^2J_{HC}$ HMBC correlations between H7' and C2' for compounds 12a/12b (FIGS. S38 and S39 in SI) unequivocally proves that the oxa-bicyclo[2.2.1]heptane ring system has been formed in the ring closure reaction (Scheme 1).

For compound 23, the upfield H2' shift at δ2.26 along with H8' at δ2.20 and their vicinal proton-proton couplings, proven by the double decoupling (FIG. S58 in SI) as well as COSY experiments (FIGS. S62 and S63 in SI), shows that the C2' substituent is the C8' methine-carbon. Strong nOe enhancement (8.6%, corresponding to ca. 2.6 Å) between H6 (thymine) and H3' (FIG. S66 in SI) in compound 23, in addition to $^3J_{H1',H2'}$=0 Hz, further confirms that the sugar is indeed locked in the North-type conformation and that the 1-thyminyl moiety is in β-configuration and anti conformation across the glycoside bond. The nOe enhancement of 3.0% for H1' upon irradiation at CH$_3$(C8')(FIG. S66 in SI) proved that the CH$_3$(C8') group is in close proximity of H1', hence the C8' chiral center is in R-configuration. Vicinal coupling of H2' with H8' as evidenced by double decoupling experiments (FIG. S58 in SI) and COSY spectra (FIGS. S62 and S63 in SI) also unequivocally showed that the bicyclo [3.2.1] octane ring system has indeed been formed in the ring-closure reaction (Scheme 2). This evidence was further corroborated by the observation of the long range $^1$H-$^{13}$C connectivity of H8' with C2', C3', and C1', that of H7' with C2' and that of H2' with CH$_3$(C8'), C7', and C8' in HMBC experiment. (FIGS. S68 and S69 in SI).

Detailed NMR characterization by 1D and 2D NMR spectra to show the fused carbocyclic nature of compounds 12a, 12b, and 23 are available in SI including chemical shifts in Tables S1 and S2 in SI, spin-spin simulations in (FIGS. S25, S27, and S59 in SI), COSY (FIGS. S30-32, S62, and S63 in SI) and TOCSY (FIGS. S33, S34, S64, and S65 in SI) to show the proton-proton connectivity, HMQC (FIGS. S37, S67 in SI) to show proton-carbon connectivity and finally HMBC (FIGS. S38, S39, S68, and S69 in SI) to establish long-range proton-carbon correlation on the basis long-range coupling constant to unequivocally prove the formation of the bicyclic system in 12a/12b as well as in 23. For the complete NMR characterization of compounds 12a/12b and 23 see Discussion S1 in SI.

5.0 Molecular Structures of Carbocyclic-LNA-T and Carbocyclic-ENA-T Based on NMR, Ab Initio and MD Calculations Initial dihedral angles from the observed $^3J_{H,H}$ couplings (Table S2 in SI) had been derived (Step I) using Haasnoot-de Leeuw-Altona generalized Karplus equation (Table S3 in SI) and utilized as constraints in the NMR constrained simulated annealing (SA) molecular dynamics (MD) simulation (0.5 ns, 10 steps) followed by 0.5 ns NMR constrained simulations using torsional constraints to yield NMR defined molecular structures of the respective compounds (for details of theoretical simulations see Experimental Section). Our combined theoretical and experimental analysis have shown that the sugar pucker conformation in 12a, 12b and 23 is indeed restricted to North-type and both the ENA- and LNA-type carbocyclic analogs have sugar moiety locked in exactly the same North-conformation as in ENA-T, aza-ENA-T, LNA-T and 2'-amino-LNA-T counterparts. Further details on the investigation of the nature of the major and minor isomers of carbocyclic-LNA-T (compounds 12a and 12b) and conformations of aglycon and 6-membered ring in carbocyclic-ENA-T (23) are provided in SI (Discussions S1 and S2 as well as in Table S3 and S4 and FIGS. S73-S75 in SI).

6.0 Synthesis and Thermal Denaturation Studies of AONs 1-17

The phosphoramidites 14 and 25 were incorporated as mono substitution in a 15 mer DNA sequence through automated synthesis on Applied Biosystems 392 RNA/DNA synthesizer for further studies. The stepwise coupling yields of the modified phosphoramidite were 96% and 98%, respectively. Dicyanoimidazole was used as the activating agent for 14, whereas tetrazole was used to activate 25 with 10 min coupling time for modified phosphoramidites, followed by de-protection of all base-labile protecting groups with 33% aqueous ammonia at 55° C. to give AONs 1-17 (Table 1). The sequence is targeted to the coding region of the SV 40 large T antigen (TAg) and has been used in the study of antisense activity of (N)-Methanocarba-T substituted oligonucleotide and as well as in the study of antisense and nuclease stability assays of oxetane modified, azetidine modified and aza-ENA modified oligonucleotides.

comparison of 6-membered carbocyclic-ENA-T with aza-ENA-T[20] counterpart has not shown any sequence dependent change in $T_m$ (+1.5° C./modification independent of the

TABLE 1

Thermal denaturation of native and modified AONs in the duplexes with complementary RNA or DNA targets[#]

| ON Sequence | $T_m$/° C. with RNA[§] | $\Delta T_m$ | $T_m$/° C. with DNA[§] | $\Delta T_m$* | MALDI-MS found/calc [M + H]+/(m/z)+ |
|---|---|---|---|---|---|
| 1. 3'-d(CTTCTTTTTACTTC)-5' | 44 | | 45 | | 4449.7/4448.7 |
| 2. 3'-d(CTT$_{(LNA)}$CTTTTTACTTC)-5' | 48 | +4 | 47 | +2 | 4475.48/4474.43 |
| 3. 3'-d(CTTCT T$_{(LNA)}$TTTTACTTC)-5' | 49 | +5 | 46.5 | +1.5 | 4475.48/4474.43 |
| 4. 3'-d(CTTCTTTT$_{(LNA)}$TTACTTC)-5' | 49 | +5 | 45.0 | 0.0 | 4475.48/4474.43 |
| 5. 3'-d(CTTCTTTTTT$_{(LNA)}$ACTTC)-5' | 49 | +5 | 46 | +1 | 4475.48/4474.43 |
| 6. 3'-d(CTT$_{(5-carbo)}$CTTTTTACTTC)-5' | 47.5 | +3.5 | 45 | 0.00 | 4489.40/4488.75 |
| 7. 3'-d(CTTCTT$_{(5-carbo)}$TTTTACTTC)-5' | 49 | +5 | 44 | −1.00 | 4489.26/4488.75 |
| 8. 3'-d(CTTCTTTT$_{(5-carbo)}$TTACTTC)-5' | 48 | +4 | 44 | −1.00 | 4489.21/4488.75 |
| 9. 3'-d(CTTCTTTTTT$_{(5-carbo)}$ACTTC)-5' | 47.5 | +3.5 | 43.0 | −2.00 | 4489.45/4488.75 |
| 10. 3'-d(CTT$_{(6-carbo)}$CTTTTTACTTC)-5' | 45.5 | +1.5 | 43.5 | −1.5 | 4503.42/4502.75 |
| 11. 3'-d(CTTCTT$_{(6-carbo)}$TTTTACTTC)-5' | 45.5 | +1.5 | 39.5 | −5.5 | 4503.25/4502.75 |
| 12. 3'-d(CTTCTTTT$_{(6-carbo)}$TTACTTC)-5' | 45.5 | +1.5 | 40.0 | −5.0 | 4503.37/4502.75 |
| 13. 3'-d(CTTCTTTTTT$_{(6-carbo)}$ACTTC)-5' | 45.5 | +1.5 | 39.5 | −5.5 | 4503.26/4502.75 |
| 14. 3'-d(CTT$_{(aza-ENA)}$CTTTTTACTTC)-5' | 48 | +4 | 44.5 | −0.5 | 4489.7/4491.1 |
| 15. 3'-d(CTTCTT$_{(aza-ENA)}$TTTTACTTC)-5' | 46.5 | +2.5 | 42.5 | −2.5 | 4489.7/4490.7 |
| 16. 3'-d(CTTCTTTT$_{(aza-ENA)}$TTACTTC)-5' | 47.5 | +3.5 | 42 | −3 | 4489.7/4490.7 |
| 17. 3'-d(CTTCTTTTTT$_{(aza-ENA)}$ACTTC)-5' | 48 | +4 | 42 | −3 | 4489.7/4490.8 |

[#]$T_m$ values measured as the maximum of the first derivative of the melting curve ($A_{260}$ vs. temperature) and are average of at least three runs recorded in medium salt buffer (60 mM Tris-HCl at pH 7.5, 60 mM KCl, 0.8 mM MgCl$_2$ and 2 mM DTT) with temperature range 20 to 70° C. using 1 μM concentrations of the two complementary strands; $\Delta T_m$ = $T_m$ relative to RNAcompliment; $\Delta T_m$* = $T_m$ relative to DNA compliment. $T_m$ performed with complementary DNA or RNA strand.
Abbreviations: T$_{(LNA)}$: LNA-T[12] compound A in FIG. 1) T$_{(5-carbo)}$: carbocyclic-LNA-T (compound 12, Scheme 1); T$_{(6-carbo)}$: carbocyclic-ENA-T (compound 23, Scheme 2); T$_{(aza-ENA)}$: aza-ENA-T.[20] (compound I in FIG. 1).

base-labile protecting groups with 33% aqueous ammonia at 55° C. to give AONs 1-17 (Table 1). The sequence is targeted to the coding region of the SV40 large T antigen (TAg) and has been used in the study of antisense activity of (N)-Methanocarba-T substituted oligonucleotide and as well as in the study of antisense and nuclease stability assays of oxetane modified, azetidine modified and aza-ENA modified oligonucleotides.

Thermal denaturation studies of AONs (Table 1) containing carbocyclic-LNA-T or carbocyclic-ENA-T have showed an increase of 3.5 to 4° C./modification (AONs 6-9 in Table 1) and 1.5° C./modification (AONs 10-13 in Table 1), respectively, for the AONs duplexes with complementary RNA. However, a net decrease of 1 to 5° C./modification has been observed for the AONs duplexes with complementary DNA. This may be due to increase in steric clash in the shallow minor groove of AON/DNA duplex. A comparative study of carbocyclic-LNA-T with LNA-T in our lab showed only ~1° C. decrease in $T_m$ with complementary RNA (Table 1) which is indeed surprising meaning that the lack of hydrophilic substituent at 2' (as in LNA) does not impart any significant decrease in duplex stability with complementary RNA. A sequence) while in the case of aza-ENA-T containing counterpart the $T_m$, significantly varied (2.5-4.0° C./modification) depending on the sequence.

7.0 Stability of the Carbocyclic-Modified AONs in the Human Blood Serum

The stability of AONs towards various exo and endo nucleases is necessary in order to develop any therapeutic oligonucleotides (antisense, RNAi, microRNA or triplexing agents). The first generation nuclease resistant antisense phosphorothioates were followed by 2'-O-alkylated modifications. Recent conformationally-constrained molecules (LNA, ENA, bicyclic, and tricyclic, aza-ENA, oxetane, azetidine etc.) have also shown enhanced nuclease stability as compared to the natural deoxy counterpart. Egli et al. have demonstrated that charge effects and hydration properties are important factors in influencing the nuclease stability of AONs with normal phosphodiester backbone. Here, we report a comparative study involving our carbocyclic-LNA (12a/12b) and carbocyclic-ENA (23) modified AONs (Table 1) with those of LNA and aza-ENA modified AONs in the human blood serum which mainly comprises of 3'-exonucleases.

Modified sequences (Table 1), $^{32}$P-labeled at 5'-ends, were digested in human blood serum at 21° C. as shown in the PAGE autoradiograms (Insets A, B, C and D in FIG. 4). In order to understand the extent of transmission of the stereoelectronic effects of the modified locked sugar to the neighboring nucleotides towards 3'- or at the 5'-end, we introduced modifications further away from the 3'-end of the AONs. The assessment of the modified AON stability in the blood serum, owing to various modifications, $T_{(LNA)}$ versus $T_{(aza-ENA)}$ versus $T_{(5-carbo)}$ versus $T_{(6-carbo)}$, vis-à-vis the native counterpart (AON 1), becomes very clear as we compare the digestions with (i) AONs 2 [with $T_{(LNA)}$], (ii) AON 6 [with $T_{(5-carbo)}$] and (iii) AON 10 [with $T_{(5-carbo)}$] and AON 14 [with $T_{(aza-ENA)}$], each having a specific single modification at the position 3 from the 3'-end (Table 1), showing that the site of the 3'-exonuclease promoted hydrolysis in blood serum was dictated by the site of the incorporation of the modification in the AON (Table 1).

The observations are as follows: (i) the modified AON 2 (full length AON='n') with $T_{(LNA)}$ at position 3 from 3'-end gave the n–1 fragment in 35 min, and n–2 fragment in 5 h as the major product, which was then completely degraded in 9 h to give various fragments ranging from n–2 to n–8 (Inset A in FIG. 4). Thus, a comparison of the blood serum cleavage pattern of the native AON 1 with that of the LNA-modified AON 2 showed that the latter is only slightly more stable than the native counterpart. (ii) On the other hand, the modified AON 14 with $T_{(aza-ENA)}$ at position 3 from 3'-end showed full hydrolysis of the 3'-terminal nucleotide within 5 h to give the AON fragments with n–1 (ca. 85%) and n–2 sequence (ca. 15%), which were further hydrolyzed to ca. 65% and 35% respectively after 12 h. No further cleavage had been observed until 48 h (Inset D in FIG. 4 and plots of percent AONs remaining as a function of time in FIG. S78 in SI). This means that AON 14 with n–1 nucleotide sequence was being hydrolyzed steadily to give the AON with n–2 nucleotide sequence. (iii) In contradistinction, the isosequencial AONs with the 5- and 6-membered carbocyclic modifications [AON 6 with $T_{(5-carbo)}$ and AON 10 with $T_{(6-carbo)}$] showed only one cleavage site to give a single AON product with n–1 nucleotide after 2 h, which remained completely stable until 48 h (PAGE autoradiograms in Insets B and C in FIG. 4 for up to 48 h, and plots of percentage AONs remaining versus time are shown in Inset A in FIG. S76 and Inset A in FIG. S77 in SI). Such blood-serum stabilities were also observed for other AONs with 5- and 6-membered carbocyclic modifications at position 6 (AONs 7/11), position 8 (AONs 8/12) and position 10 (AONs 9/13), (PAGE autoradiograms in Insets B and C in FIG. 4, and plots in Insets B-D in FIGS. S76 and S77 in SI) as well as for aza-ENA-T containing AONs (15/16/17), (PAGE autoradiograms in Inset D, FIG. 4 and plots in Insets B-D in FIG. S78). The plots (FIGS. S76 and S77 in SI) obtained as a result of quantification of the PAGE autoradiograms (FIG. 4) in carbocyclic modified AONs 6 (Inset B in FIG. 4) and 10 (Inset B in FIG. 4) clearly showed that the resistance towards nucleases was transmitted towards the neighboring 3' nucleotide of the carbocyclic modification site (i.e., n–1 fragment, when n=full length 15 mer AON and the carbocyclic modification site is at position 3 from 3'-end). In contrast, with the aza-ENA modified AON 14 (Inset D in FIG. 4, FIG. S78 in SI) where the hydrolysis proceeded both at the 3'-phosphate of the modification site as well as that of the 3'-neighbor, giving first n–1 fragment as the predominant product, which was further hydrolyzed with time giving the n–2 fragment (when n=full length 15 mer AON and the aza-ENA modification site is at position 3 from 3'-end). The residual fragments so formed was stable against further hydrolysis for up to 48 h.

Similar results were obtained for AONs 7-9 (5-membered carbocyclic modifications at position 6, 8 and 10 from 3'-end giving n–4, n–6 and n–8 fragments, respectively, FIG. S76 in SI), AONs 11-13 (6-membered carbocyclic modifications at position 6, 8 and 10 from 3'-end giving n–4, n–6 and n–8 fragments, respectively, FIG. S77 in SI) and AONs 15-17 (6-membered aza-ENA modifications at position 6, 8 and 10 from 3'-end giving n–4/n–5, n–6/n–7 and n–8/n–9 fragments, respectively. FIG. S78 in SI). The fact that in case of 5- and 6-membered carbocyclic modifications, the 3'-phosphate of the modified nucleotide was fully stable, whereas the 3'-phosphate of the neighboring residue, which is next to the modified nucleotide at 3'-end, was unstable and fully hydrolyzed, compared to that of aza-ENA modification in which both the 3'-phosphates of the modified nucleotide as well as that of the neighbor residue were unstable, shows that the stereoelectronic effect of the locked sugar into the N-type conformation (carbocyclic versus aza-ENA) at the modification site is transmitted differently to alter the phosphate backbone torsions towards the 3'-end thus modulating its susceptibility differently towards the hydrolytic cleavage by 3'-nucleases. It is noteworthy that the transmission of stereoelectronic effect in aza-ENA-T is very comparable to those for oxetane-T modified and azetidine-T modified isosequential AONs 7.1 Mechanism of the Modified AON Stability in the Blood Serum 7.1.1 Effect of 2'-Heteroatom Versus 2'-Carbo Substitution in the Modified Nucleotide in the AON.

The 3'-terminal nucleotide is hydrolyzed by 3'-exonuclease in AON substituted by the 5- or 6-membered carbocyclic residue at position 3 (AONs 6 and 10) to give only the n–1 fragment. In AONs with single substitution at either position 6 (AONs 7 and 11) or 8 (AONs 8 and 12) or 10 (AONs 9 and 13), similarly gives only n–4, n–6 or n–8 fragments, respectively. The residual AON sequences remained at the 5'-end of the modification site were found to be intact for more than 48 h in the human blood serum (see PAGE autoradiograms in Insets: B-C in FIG. 4, and for plots of percentage of oligonucleotide left as a function time in Insets: A-D in FIGS. S76 and S77 in SI). However AONs containing a single 6-membered aza-ENA-T substitution (i.e. AONs 14-17 with single modification incorporated at position 3, 6, 8 and 10, respectively) showed progressive cleavage with time until the site of modification (FIG. 4, Inset D and for plot of percentage of oligonucleotide left as a function time in Insets: A-D in FIG. S78 in SI).

This was an interesting observation since the isosequential North-constrained 1',2'-oxetane[17] or 1',2'-azetidine[18] with identical modification site exhibited the 3'-exonuclease promoted 3'-O—P bond hydrolysis right at the 3'-end of the modification site itself (i.e at the n–2 site). In contradistinction, isosequencial AON with aza-ENA-T modification at position 3 from 3'-end (i.e AON 14) gives predominantly AON with n–1 residue (FIG. 4, Inset D), which steadily hydrolyzes to give the n–2 product but the corresponding carbocyclic AONs (AONs 6 and 10) give only the fully-stable n–1 fragment. This suggests that the enzymes of human serum recognize and confer different grades of stability against hydrolysis for relatively more flexible 1',2'-conformational constraint as in 1',2'-oxetane[17] or 1',2'-azetidine compared to the stronger conformational constraints imposed by 2',4'-modifications as in aza-ENA or in 5- and 6-membered carbocyclic-ENA/LNA.

Interestingly, a single modification of AON with our carbocyclic-LNA-T or with carbocyclic-ENA-T nucleotides at position 3 from the 3'-end in to the AON 6 or AON 10 has provided the highest degree of exonuclease stability which was earlier achieved by employing four 2'-O-[2-(guanidinium)ethyl] (2'-O-GE) modifications (including the 3'-terminal modification). Other carbocyclic modifications have also shown nuclease resistance, but less efficiently. The 2'- or 6'-alkoxy substituted carbocyclic nucleotide units (three units at the 3'-end) in the modified AON enhanced stability of AON on fetal calf serum from 2.5 times for [6'α-carbocyclic-2'-deoxy]-T substitution to 24 times for [6'α-carbocyclic-2'-O—$(CH_2)_4$—$NH_2$ or 2'-O—$(CH_2)_3$-Ph]-T substitution), compared to that of the native.[83] It was suggested that replacement of substituents involved in natural enzyme-substrate complex results in poor recognition and processing by the nucleolytic enzymes, thereby resulting in the nuclease stability. Thus, the nuclease stability was enhanced when 2'-bulky substituent was introduced in the carbocyclic nucleosides Subsequently, it was proved that the native ribonucleoside with 2'-O-alkyl substituent either by its bulk or by its stereoelectronic modulation of the hydration can bring about nucleolytic stability.

The AONs containing 5-membered carbocyclic-LNA versus AONs with the 6-membered carbocyclic-ENA show enhanced, but identical, blood serum stability, thereby showing that the steric bulk is relatively unimportant. This is in sharp contrast to the conclusion drawn by comparison of the LNA versus ENA modified AONs, in that the latter is 2.5-3 times more stable than the former,[13] apparently, according to the authors, owing to an extra methylene linker. The 3'-exonuclease (SVPDE) stability had also been observed to be higher for the 2'-O-GE and 2'-O-aminopropyl modifications, as well as for the 4'-α-C-aminoalkylthymidine AONs, which showed complete nuclease resistant upon incorporation of five modified nucleotides as mixmers, compared to the native counterpart. Notably, nuclease digestion studies involving 4'-α-C-aminoalkylthymidine AONs showed that longer chain alkyls were less potent in providing stability against nuclease, and hinted at the role of ammonium ions in providing the stability[30]. Subsequently, it was shown that the native ribonucleoside with 2'-O-alkyl substitutent either by its bulk (pentoxy>propoxy>methoxy>deoxy) or by its stereoelectronic modulation (2'-O-GE) of the hydration can bring about nucleolytic stability.

Since our carbocyclic AONs were completely devoid of polar effect at C2', the above explanations invoking charge or steric effects is not applicable to explain the unprecedented nuclease stability of these carbocyclic AONs in the blood serum. The enhanced stabilities of the carbocyclic-AONs with respect to their bicyclic 2'-O-(LNA and ENA) and aza-ENA analogs suggests that the accessibility of water to the 2'-O— in LNA or to the 2'-N— in aza-ENA substituent in a modified nucleotide is most probably more important in order to cleave the vicinal 3'-phosphodiester bond by the exonucleases of the blood serum.

7.1.2 Solvation Free-Energy Calculation to Elucidate Relative Hydrophobicity of the 2'-Substituent.

In order to understand how the nature of 2'-substitution in the modified AON affects the relative access of water to the scissile phosphate, we have analyzed the solvation free-energies of different modified nucleosides (Table S5 in SI) utilizing Baron and Cossi's implementation of the polarizable conductor CPCM model[85] of solvation on the ab initio optimized (HF, 6-31G** basis set) molecular geometries. This allowed us to understand the lipophilic versus hydrophilic nature of different 2',4'-constrained modifications in LNA/ENA/2'-amino-LNA/aza-ENA/carbocyclic-LNA/carbocyclic-ENA in a comparative manner. Table S5 in SI thus shows that the energy of stabilization of the solvated of 5-membered (12a and 12b) and 6-membered (23) carbocyclic nucleosides compared to their oxygen and nitrogen containing counterparts decreases in the following order: 6-membered carbocyclic-ENA-T (12.2 kcal $mol^{-1}$)>. 5-membered carbocyclic-LNA-T (12.9 kcal $mol^{-1}$)>aza-ENA-T (15.2 kcal $mol^{-1}$)> ENA-T (15.6 kcal $mol^{-1}$)>LNA-T (16.8 kcal $mol^{-1}$). This suggests that our the 5-membered and 6-membered carbocyclic nucleosides, on account of their hydrophobic nature, are not as well solvated as compared to their LNA, ENA and aza-ENA counterparts, thereby showing that hydration around a scissile phosphate is most probably important for the nuclease promoted hydrolysis. This leads us to speculate that this hydration around C2' substituent with heteroatoms such as 2'-O— in LNA or to the 2'-N— in aza-ENA in a modified AON is utilized by the exonuclease to capture a water molecule to hydrolyze the 3'O—$PO_3^-$R bond of the vicinal phosphate, which is not possible with our carbocyclic-AONs.

8.0 3'-Exonuclease Stability Assay (with Snake Venom Phosphodiesterase):

The stability of AONs of carbocyclic analogs of LNA and ENA (Table 1) towards 3'-exonuclease was investigated using snake venom phosphodiesterase over a period of 72 h at 21° C. (PAGE autoradiogram in FIG. S79 in SI) and compared with isosequential LNA and aza-ENA modified AONs under identical conditions. The results obtained were similar to that obtained in human blood serum assay (PAGE autoradiogram in FIG. 4) showing identical cleavage sites and identical resistance pattern i.e. cleavage of phosphodiester bond next to modification site towards 3' end and subsequent resistance to degradation for up to 72 h (PAGE autoradiogram in FIG. S79 in SI and plots of percentage of oligonucleotide left as function of time in FIGS. S80-S82 in SI). These experiments clearly show that the effect of hydrophobic environment imparted by the carbocyclic analogs of LNA and ENA is important in dictating the nuclease stability of the modified AON.

9.0 RNase H Digestion Studies

In the antisense strategy, the RNase H recruitment by the modified AON, with long nuclease stability as exhibited by our carbocyclic modifications, and the target RNA heteroduplexes is an important step for the design of potential therapeutics for engineering specific gene silencing effect.[2]

Hence, RNase H mediated cleavage of the RNA strand complementary to the modified AON strands 2-17 (with carbocyclic-LNA, carbocyclic-ENA, aza-ENA and LNA modifications) has been studied here, using the native AON/RNA duplex as a reference, in order to address the issue if the recruitment of RNase H by the heteroduplexes is in anyway compromised as a result of carbocyclic modifications incorporated in the AON strand. We have used *E. coli* RNase H in our studies on account of its availability, and the fact that its properties are known to be not very different from the mammalian enzyme.[77] The, RNA complementary to AONs (AONs 1-17 in Table 1) formed duplexes and were found to be good substrates for RNase H but with varying cleavage sites (FIG. 5) depending on the site of modification in the AON strand as shown in PAGE autoradiograms (Insets A-D in FIG. 6). The main observations are as follows:

(i) The RNA compliment of the unmodified native AON 1/RNA duplex was cleaved quite randomly with a slight preference after A-8 position.

(ii) For the isosequential AONs with single modification at different sites (Table 1) containing either LNA (AONs 2-5), carbocyclic-LNA-T (AONs 6-9), carbocyclic-ENA-T (AONs 10-13) or aza-ENA-T AONs 14-17) modifications showed uniquely identical cleavage footprint patterns having 5-6 nt gaps (Insets A-D in FIG. 6). It is remarkably surprising that the RNase H enzyme, could not distinguish the functional differences exhibited by the North-conformationally constrained LNA, carbocyclic-LNA, carbocyclic-ENA, and aza-ENA modifications, compared to nucleases.

This suggests that the RNase H does not recognize the hydrophobic (as in carbocyclic-LNA, carbocyclic-ENA) or hydrophilic (LNA and aza-ENA) character of the substituent at the 2'-position of the modified nucleosides, but interrogates only at the subtle difference in the flexibility of the North-type sugar puckering (2',4' versus 1',2') in that we observed different cleavage sites and footprint pattern (4-5 nt gaps) for isosequencial 1',2'-constrained North-East sugar puckered oxetane and azetidine modified AONs compared to those of the more rigid 2',4'-constrained systems (LNA, carbocyclic-LNA, carbocyclic-ENA and aza-ENA modified AONs).

The cleavage rates of RNase H digestion were determined by densitometric quantification of gels and subsequently by plotting the uncleaved RNA fraction as a function of time (Insets E-H in FIG. 6). The reaction rates were obtained by fitting the degradation curves to single-exponential decay functions. The relative cleavage rates with carbocyclic-LNA, carbocyclic-ENA, aza-ENA and LNA modified AON/RNA duplexes were found to be very similar to that of the native counterpart irrespective of the type and the site of modification in the AON strand (compare the relative rates in FIG. 14).

The main conclusion which can be drawn from these studies is that even though all AONs used (Table 1) recruited RNase H almost as efficiently as that of the native counterpart (FIG. 7), but it is only the carbocyclic-LNA and the carbocyclic-ENA modified AONs (AON 6-13) which have shown (FIG. 4), much enhanced nuclease stability in the blood serum (ca 48 h) as compared to that of the native and the LNA-modified AONs (fully degraded <12 h) and aza-ENA (≈85% stable in 48 h) (FIG. 8, FIGS. S76-S78 in SI). Clearly, the enhanced life-time of these carbocyclic-modified AONs in the blood serum (FIG. 8, FIGS. S76-S78 in SI) may produce the highly desired pharmacokinetic properties because of their stability, and consequently a net reduction of the required dosage. This makes our carbocyclic-LNA, carbocyclic-ENA, and aza-ENA modified AONs best candidates for the antisense therapeutics because of their efficient exploitation in the enzymatic turn-over. In this context, it may be noted that the modified AONs with all thymidines replaced with the conformationally-constrained (North- or South-locked) 2'-deoxy-methanocarba-nucleoside or LNAs or tricyclo-DNA did not recruit RNase H.

CONCLUSIONS

1. In order to develop gene silencing agents with natural phosphodiester linkages, three factors are perhaps most important: Stability, Delivery and RNase H recruitment. In this regard, we have designed and synthesized AONs containing 5-membered (12a/12b) and 6-membered (23) carbocyclic analogs of LNA (carbocyclic-LNA-T) and ENA (carbocyclic-ENA-T), which are both nuclease resistant and capable of eliciting RNase H response.
2. The synthesis of these novel conformationally constrained carbocyclic analogs have been achieved using free-radical C—C bond formation as a key step. Various NMR experiments including $^1$H homodecoupling experiments, 1D nuclear Overhauser effect spectroscopy (1D NOESY), 2D total correlation spectroscopy (TOCSY), 2D COSY, and $^{13}$C NMR experiments, including distortionless enhancement by polarization transfer (DEPT), as well as long-range $^1$H-$^{13}$C HMBC correlation ($^2J_{H,C}$ and $^3J_{H,C}$), and one-bond heteronuclear multiple-quantum coherence (HMQC) have been employed to show unambiguously that indeed a Carbon-Carbon formation has taken place between C2' and the olefinic side chain tethered at C4' to give the North-type conformationally constrained bicyclic nucleosides.
3. The molecular structures of the 5-membered (12a/12b) and 6-membered (23) carbocyclic analogs have also been studied using ab initio and MD simulations to understand the structural reasons behind the regio- and stereochemistry of the cyclization products.
4. Sixteen single modified AONs (15mer) containing the carbocyclic analogs (carbocyclic-LNA-T and carbocyclic-ENA-T) and aza-ENA[20] modification have been tested and have shown good target affinity as shown by the increase (compared to the native counterpart) in thermal stability of duplexes with their complementary RNAs ($T_m$ increase by 3.5-5° C. and 1.5° C./modification) for carbocyclic-LNA-T and carbocyclic-ENA-T respectively.
5. The AONs containing the carbocyclic analogs of ENA and LNA have shown unprecedented nuclease stability, starting from the 3'-neighboring nucleotide of the modification site till the 5'-end, thus the nuclease stable part of the AON depends upon where the site of the modification is introduced in the modified AON.
6. The modified AONs have shown recruitment of RNase H almost as efficiently as by native deoxy/RNA duplexes and brought about degradation of the RNA target.
7. A comparison of the nuclease stability of carbocyclic analogs with LNA and aza-ENA and its correlation with the energy of solvation indicates that it is the relative hydrophobicity of the carbocyclic modification leading to a change of hydration pattern around the modified nucleotide in the AONs which is probably responsible for the high nuclease stability of the modified AONs.

Implication

Remarkably, a single incorporation of carbocyclic-LNA/-ENA-T into AONs leads to very much more enhanced nuclease stability in the blood serum (stable >48 h) [compared to those of the native (fully degraded <3 h) and the LNA-modified AONs (fully degraded <9 h) and aza-ENA (≈85% stable in 48 h)]. This enhanced stability of the carbocyclic-LNA/-ENA-T containing AONs however do not compromise the recruitment of the RNase H to cleave the complementary RNA in the modified AON/RNA heteroduplex, compared to that of the native. This enhanced life-time of these carbocyclic-modified AONs in the blood serum may produce the highly desired pharmacokinetic properties and consequently a reduction of the required dosage and the toxicity while down-regulating a message in vivo, which may make the carbocyclic-LNA and carbocyclic-ENA modifications excellent candidates as potential antisense or RNAi therapeutic agent.

EXPERIMENTAL SECTION 3,5-Di-O-benzyl-4-C-vinyl-1,2-O-isopropylidine-α-D-ribofuranose (4)

Oxalyl chloride (10.7 mL, 125 mmol) was added to dichloromethane (350 mL) cooled at −78° C. DMSO (15 mL, 200 mmol was added dropwise to this solution in about 30 min. After stirring for 20 more min a solution of 2 (20 g, 50 mmol) in dichloromethane (100 mL) was added dropwise to this mixture in about 20 min and left to stir at −78° C. for another 30 min. DIPEA (60 mL, 350 mmol) was added to this cooled mixture and allowed to warm to room temperature. Water was added to the reaction and twice extracted with dichloromethane (100 mL). The organic layer was washed with water and brine, dried over MgSO$_4$ and concentrated under reduced pressure. In another reaction BuLi (1.6 molar solution in hexane, 95 mL, 150 mmol) was added to a pre-cooled suspension of methyl-triphenylphosphonium bromide (54 g 150 mmol) at 0° C. in dry THF and allowed to stir at room temperature for 1 h. The yellow solution so obtained was cooled to −78° C. and a solution of crude aldehyde in dry THF was then added dropwise in about 20 min and left to stir at −78° C. overnight. The reaction was quenched with saturated aqueous NH$_4$Cl, and stirred for about 1 h at room temperature and then extracted with ether (3×200 mL) dried over MgSO$_4$ and concentrated under reduced pressure. The crude material was purified by column chromatography on silica gel (0-10% ethyl acetate in cyclohexane, v/v) to give 2 as a colorless oil (17 g, 43 mmol, 87%). R$_f$=0.60 (20% ethyl acetate in cyclohexane, v/v). $^1$H NMR (600 MHz, CDCl$_3$) δ: 7.3 (10H, m), 6.20 (1H, dd, J$_{H6,H7}$=11 Hz, 18 Hz, H6), 5.76 (1H, d, J$_{H1,H2}$=3.9 Hz, H1), 5.22 (1H, dd, 1.8 Hz, 17.5 Hz, H7), 5.25 (1H, dd, J=1.8 Hz, 11 Hz, H7), 4.76 (1H, d, J$_{gem}$=12 Hz, CH$_2$Bn), 4.59 (1H, d, J$_{gem}$=12 Hz, CH$_2$Bn), 4.57 (1H, app t, J=4.6 Hz, H2), 4.5 (1H, d, J$_{gem}$=12 Hz, CH$_2$Bn), 4.40 (1H, d, J$_{gem}$=12 Hz, CH$_2$Bn), 4.25 (1H, d, J=4.9 Hz, H3), 3.32 (2H, s, H5), 1.52 (3H, s, CH$_3$), 1.28 (3H, s, CH$_3$); $^{13}$C NMR (125.7 MHz) δ: 138.0, 137.8, (Bn), 135.4 (C6), 128.3, 127.9, 127.8, 127.5 (aromatic), 116.3 (C7), 113.3, 103.8 (CD, 86.4 (C4), 78.3 (C2), 77.2 (C3), 73.4 (CH$_2$Bn), 72.7 (C5), 72.4 (CH$_2$Bn), 26.0 (CH$_3$), 25.6 (CH$_3$).

3,5-Di-O-benzyl-4-C-hydroxyethyl-1,2-O-isopropylidine-α-D-ribofuranose (5)

To a solution of 2 in dry THF (200 mL) was added 0.5 molar solution of 9-BBN (250 mL, 128 mmol) and stirred overnight. Water was added till gas evolution stopped, 3N NaOH solution (50 mL) was added and then slowly 33% aqueous H$_2$O$_2$ was added while temperature was maintained at about 50° C. The mixture was stirred for about 30 min at room temperature and then partitioned between ethyl acetate and water and extracted twice with ethyl acetate (100 mL). The organic layer was dried, evaporated and purified over silica gel (20-30% ethyl acetate in cyclohexane, v/v) to give 5 as colorless oil (16 g, 39 mmoles, 95%). R$_f$=0.40 (5% methanol in dichloromethane, v/v). $^1$H NMR (270 MHz, CDCl$_3$) δ: 7.3 (10H, m), 5.75 (1H, d, J$_{H1,H2}$=4 Hz, H1), 4.77 (1H, d, J$_{gem}$=12 Hz, CH$_2$Bn), 4.67 (1H, app t, J=4.8 Hz, H2), 4.55 (1H, d, J$_{gem}$=12 Hz, CH$_2$Bn), 4.52 (1H, d, J$_{gem}$=12 Hz, CH$_2$Bn), 4.41 (1H, d, J$_{gem}$=12 Hz, CH$_2$Bn), 4.12 (1H, d, J$_{H2,H3}$=5.57 Hz, H3), 3.8 (2H, m, H7), 3.51 (1H, d, J=10.3 Hz, H5), 3.3 (1H, d, J=10.4 Hz, H5), 3.0 (1H, br s, 7-OH), 2.51 (1H, ddd, J=3.4 Hz, 6.4 Hz, 15 Hz, H6), 1.80 (1H, ddd, J=4 Hz, 8.5 Hz, 15 Hz, H6), 1.63 (3H, s, CH$_3$), 1.31 (3H, s, CH$_3$); $^{13}$C NMR (67.9 MHz, CDCl$_3$) δ: 137.9 (Bn), 127.7, 127.8, 127.9, 128.5 (aromatic), 113.6 (isopropyl), 104.4 (C1), 87.3 (C4), 79.3 (C2), 78.6 (C3), 73.6 (CH$_2$Bn), 73.3 (C5), 72.5 (CH$_2$Bn), 58.8 (C7), 34.0 (C6), 26.5 (CH$_3$), 26.4 (CH$_3$); MALDI TOF m/z [M+Na]$^+$ found 437.14, calc 437.19.

4-C-Allyl-3,5-di-O-benzyl-1,2-O-isopropylidine-α-D-ribofuranose (6)

Oxalyl chloride (6.2 mL, 72.46 mmol) was added to dichloromethane (200 mL) cooled at −78° C. DMSO (11 mL, 145 mmol) was added dropwise to this solution in about 30 min After stirring for 20 more min a solution of 5 (15 g, 36.23 mmol) in dichloromethane (100 mL) was added dropwise to this mixture in about 20 min and left to stir at −78° C. for another 45 min. DIPEA (35 mL, 200 mmol) was added to this cooled mixture and allowed to warm to room temperature. Water was next added to the reaction and twice extracted with dichloromethane (100 mL). The organic layer was washed with water and brine, dried over MgSO$_4$ and concentrated under reduced pressure. In another reaction BuLi (1.6 molar solution in hexane, 78 mL, 126 mmol) was added to a pre-cooled suspension of methyl-triphenylphosphonium bromide (45 g, 126 mmol) at 0° C. in dry THF and allowed to stir at room temperature for 1 h. The yellow solution so obtained was cooled to −78° C. and a solution of crude aldehyde in dry THF was then added dropwise in about 20 min and left to stir at −78° C. overnight. The reaction was quenched with saturated aqueous NH$_4$Cl, and stirred for about 1 h at room temperature and then extracted with ether (3×200 mL), dried over MgSO$_4$ and concentrated under reduced pressure. The crude material was purified by column chromatography on silica gel (0-10% ethyl acetate in cyclohexane, v/v) to give 6 as yellowish oil (12 g, 29 mmol, 70%). R$_f$=0.60 (20% ethyl acetate in cyclohexane, v/v). $^1$H NMR (270 MHz, CDCl$_3$) δ: 7.35 (10H, m, Bn), 5.95 (1H, m, H7), 5.77 (1H, d, J$_{H1,H2}$=4 Hz, H1), 5.09 (2H, m, H8), 4.78 (1H, J$_{gem}$=12.1 Hz, CH$_2$Bn), 4.63 (1H, app t, J=4.3 Hz, H2), 4.58 (1H, d, J$_{gem}$=12.1 Hz, CH$_2$Bn), 4.54 (1H, d, J$_{gem}$=12 Hz, CH$_2$Bn), 4.41 (1H, d, J$_{gem}$=12 Hz, CH$_2$Bn), 4.18 (1H, d, J$_{H2,H3}$=5.2 Hz, H3), 3.45 (1H, d, J$_{H6,H6}$=10.4 Hz, H5), 3.32 (1H, d, J$_{H5,H5}$=10.4 Hz, H5), 2.96 (1H, dd, J$_{H6,H6}$=14.7 Hz, J$_{H6,H7}$=7.4 Hz, H6), 2.39 (1H, dd, J$_{H6,H6}$=14.7 Hz, J$_{H6,H7}$=8.5 Hz, H6), 1.60 (3H, s, CH$_3$), 1.33 (3H, s, CH$_3$); $^{13}$C NMR (67.9 MHz) δ: 138.3 (Bn), 134.0 (C7), 127.6, 127.8, 128.4, 128.6 (aromatic), 117.6 (C8), 113.3 (isopropyl), 104.2 (C1), 86.4 (C4), 79.6 (C2), 78.3 (C3), 73.5 (CH$_2$Bn), 72.5 (C5), 72.3 (CH$_2$Bn), 37.0 (C6), 26.8 (CH$_3$), 26.3 (CH$_3$); MALDI-TOF m/z [M]$^+$ Found 410.2, calcd 410.1.

1-[4-C-Allyl-3,5-di-O-benzyl-2-O-acetyl-β-D-ribofuranosyl]-thymine (8)

Acetic anhydride (17 mL, 175 mmoles) and acetic acid (87 mL) were added to 4 (6.0 g, 14 mmoles) and cooled, triflic acid (0.1 mL, 0.7 mmoles) was added to it and stirred. After 30 min the reaction was quenched with cold saturated NaHCO$_3$ solution and extracted with dichloromethane. The organic layer dried and evaporated. The crude was co evaporated with dry CH$_3$CN thrice and dissolved in the same. Thymine (2.4 g, 19 mmol) and N,O-bis(trimethylsilyl)acetamide (9.6 mL, 38 mmol) was added to this solution and refluxed for 45 min till suspension becomes a clear solution. This solution was cooled to 0° C. and TMSOTf (3.5 mL, 17.5 mmol) was added dropwise and left to stir overnight. The reaction was quenched with saturated NH$_4$Cl solution and extracted with dichloromethane The organic layer dried, evaporated and chromatographed over silica gel (2-6% methanol in dichloromethane, v/v) to give 8 as white foam (6 g, 11 mmol, 80%). R$_f$=0.60 (5% methanol in dichloromethane, v/v). $^1$H NMR (500 MHz) δ: 7.48 (1H, s, H6), 7.3 (10H, m), 6.25 (1H, d, J$_{H1',H2'}$=5.5 Hz, H1'), 5.83 (1H, m, H7'), 5.41 (1H, app t, 5.5 Hz, H2'), 5.09 (2H, m, H8', 8''), 4.63 (1H, d, J$_{gem}$=11.5 Hz, CH$_2$Bn), 4.50 (1H, d, J$_{gem}$=11.5 Hz, CH$_2$Bn), 4.47 (1H, d, J$_{gem}$=11.5 Hz, CH$_2$Bn), 4.45 (1H, d, J$_{gem}$=11.5 Hz, CH$_2$Bn), 4.37 (1H, d, J$_{2H',3H'}$=5.94 Hz, H3'), 3.67 (1H, d, J$_{H5',H5''}$=10.5 Hz, H5''), 3.38 (1H, d, J$_{H5',H5''}$=10.5 Hz, H5'), 2.65 (1H, dd, J$_{H6,H7}$=6 Hz, J$_{H6',H6''}$=15 Hz, H6''), 2.29 (1H, dd, 8 Hz, 14 Hz, H6'), 2.08 (3H, acetyl), 1.49 (3H, CH$_3$-thymine); $^{13}$C NMR (125.7 MHz) δ: 170.1 (>C=O acetyl), 163.9 (C4), 150.5 (C2), 135.6, 137 2, 137.5 (aromatic), 132.5 (C6), 127.6, 127.8, 128.0, 128.0, 128.4, 128.6 (aromatic), 118.6 (C8'), 111.3 (C5), 86.9 (C4'), 85.9 (C1'), 77.6 (C3'), 75.1 (C25, 74.3 (CH$_2$Bn), 73.5 (CH$_2$Bn), 72.9 (C5'), 37.2 (C6'), 20.7 (CH$_3$, acetyl), 11.9 (CH$_3$, thymine): MALDI-TOF m/z [M+H]$^+$ found 521.14 calcd 521.22.

1-[4-C-Allyl-3,5-di-O-benzyl-2-O-phenoxythiocarbonyl-β-D-ribofuranosyl]-thymine (10)

Compound 8 (5.0 g, 9.6 mmol) was treated with 27% methanolic ammonia solution overnight. After evaporation of the solvent the crude was coevaporated thrice with dry pyridine and dissolved in the same. To this pre-cooled solution was added DMAP (1.17 g, 9.6 mmol) and then dropwise was added phenyl chlorothionoformate (1.6 mL, 11.53 mmol) and reaction stirred overnight. Reaction was quenched with saturated solution of NaHCO$_3$ and extracted with dichloromethane. The organic layer was dried over MgSO$_4$, concentrated and chromatographed over silica gel (10-30% ethyl acetate in cyclohexane, v/v) to give 10 as yellowish foam (4.1 g, 6.72 mmol, 70%). R$_f$=0.60 (30% ethyl acetate in cyclohexane, v/v). $^1$H NMR (600 MHz) δ: 8.58 (1H, s, N—H), 7.48 (1H, s, H6), 7.19 (15H, m), 6.44 (1H, d, J$_{H1',H2'}$=6.1 Hz, H1'), 5.97 (1H, app t, J=5.8 Hz, H2'), 5.83 (1H, m, H7'), 5.09 (2H, m, H8'-H8"), 4.77 (1H, d, J$_{gem}$=11.2 Hz, CH$_2$Bn), 4.55 (3H, m, CH$_2$Bn, H3'), 3.71 (1H, d, J$_{H5',H5''}$=10.3 Hz, H5"), 3.48 (1H, d, J$_{H5',H5''}$10.3 Hz, H5'), 2.66 (1H, dd, J$_{H6,H6}$=14.6 Hz, J$_{H6,H7}$=8.1 Hz, H6"), 2.35 (1H, dd, J$_{H6,H6}$=14.6 Hz, J$_{H6,H7}$=8.1 Hz, H6'), 1.51 (3H, CH$_3$, thymine); $^{13}$C NMR (125.7 MHz) δ: 194.4 (>C=S), 163.4 (C4), 150.3 (C2), 137.1, 137.2 (aromatic), 135.6 (C6), 132.4 (C7'), 121.6, 126.7, 127.3, 127.6, 127.8, 128.0, 128.1, 128.4, 128.6, 129.3, 129.5 (aromatic), 118.8 (C8'), 111.5 (C5'), 87.1 (C4'), 85.1 (C2'), 82.9 (C1'), 77.8 (C3'), 74.9 (C—CH$_2$Bn), 73.7 (C5'), 73.7 (C—CH$_2$Bn), 37.3 (C6'), 11.9 (CH$_3$, thymine); MALDI-TOF m/z [M+H]$^+$ found 615.16 calcd 615.21.

(1R,3R,4R,5R,7S)-7-Benzyloxy-1-benzyloxymethyl-3-(thymin-1-yl)-2-oxa-bicyclo[2.2.1]heptane (11a/11b)

Compound 10 (3.0 g, 4.8 mmol) was dissolved in 150 mL of dry toluene and purged with dry nitrogen for 30 min Bu$_3$SnH (1.3 mL, 4.8 mmol) was dissolved in 20 mL of toluene and half of this solution was added dropwise to refluxing solution in over 30 min. AIBN (0.920 g, 4.8 mmol) was dissolved in 20 mL of dry toluene and added to the above solution dropwise and simultaneously was added the remaining solution of Bu$_3$SnH in around 60-70 min. After 60 min of reflux, the solution was cooled and CCl$_4$ (10 mL) was added, and stirred for 20 min. A solution of iodine in dichloromethane was added to the above solution until a faint coloration persists and solvent was evaporated. The solid so obtained was taken in ethyl acetate and repeatedly washed with saturated aqueous solution of potassium fluoride till white flocculent precipitate is seen the organic layer was dried evaporated and chromatographed over silica gel (10-60% ethyl acetate in cyclohexane, v/v) to give a diastereomeric mixture 11a/11b in 73% yield (1.6 g, 3.5 mmol). R$_f$=0.40 (30% ethyl acetate in cyclohexane, v/v).$^{13}$C NMR (125.7 MHz) δ: 163.8, 149.7, 137.7, 137.4, 136.3, 136.2, 128.5, 128.4, 128.3, 127.8, 127.7, 127.7, 127.6, 127.4, 109.0, 88.8, 88.6, 84.1, 78.6, 78.1, 77.1, 73.6, 71.9, 71.7, 67.5, 67.4, 47.9, 47.8, 38.6, 37.6, 33.5, 28.7, 20.0, 15.4, 12.0, 11.9; MALDI-TOF m/z [M+H]$^+$ found 463.11 calcd 463.22.

(1R,3R,4R,5R,7S)-7-Hydroxy-1-hydroxymethyl-3-(thymin-1-yl)-2-oxa-bicyclo[2.2.1]heptane (12)

To a solution of 11a/11b (1.5 g, 3.24 mmol) in dry methanol, 20% Pd(OH)$_2$/C (1.6 g) ammonium formate (4.0 g, 65 mmol) was added and put to reflux. The same amount of ammonium formate and 20% Pd(OH)$_2$/C was added twice after 3 hours and reaction left to reflux for 8 h. After the reaction was finished as seen by TLC the suspension was filtered over celite and organic phase evaporated and chromatographed over silica gel (2-7% methanol in dichloromethane, v/v) to obtain 12a/12b (0.70 g, 2.4 mmol, 76%) as white powder. R$_f$=0.50 (7% methanol in dichloromethane, v/v).$^1$H NMR (600 MHz, D$_2$O) of 12a δ: 7.81 (1H, s, H6, thymine), 5.78 (1H, s, H1'), 4.18 (1H, d, 4.4 Hz, H3'), 3.85 (1H, d, J$_{H5',5''}$=12.6 Hz, H5'), 3.83 (1H, d, J$_{H5',5''}$=12.6 Hz, H5"), 2.65 (1H, m, H7'), 2.43 (1H, d, J$_{H2',H7}$=4.4 Hz, H2'), 2.04 (1H, dd, J$_{H6',H6''}$=12.3 Hz, J$_{H7',H6''}$=10.6 Hz, H6"), 1.89 (3H, d, J=1.25 Hz, thymine CH$_3$), 1.23 (3H, d, J$_{H7',CH3}$=7.3 Hz, C7'-CH$_3$), 1.17 (1H, dd, J$_{H6',H6''}$=12.3 Hz, J$_{H7',H6''}$=4.9 Hz, H6'); $^{13}$C NMR (125.7 MHz, D$_2$O) δ: 166.64 (C4), 151.05 (C2), 137.33 (C6), 109.7 (C5), 90.6 (C4'), 83.7 (C1'), 71.7 (C3'), 58.7 (C5'), 49.7 (C7'), 36.0, (C6'), 28.1 (C7'), 14.4 (C7'-methyl) 11.5 (thymine CH$_3$); MALDI-TOF m/z [M+H]$^+$ found 283.94, calcd 283.14.

(1R,3R,4R,5R,7S)-7-Hydroxy-1-(4,4'-dimethoxytrityloxymethyl)-3-(thymin-1-yl)-2-oxa-bicyclo[2.2.1]heptane (13)

Compound 12 (0.70 g, 2.4 mmol) was evaporated twice with dry pyridine and suspended in the same. 4,4'-dimethoxytrityl chloride (1.26 g, 3.7 mmol) was added and stirred overnight. Reaction was quenched with saturated aqueous NaHCO$_3$ and extracted thrice with dichloromethane (50 mL). The organic phase was dried, evaporated and chromatographed over silica gel (1% pyridine/ethyl acetate in cyclohexane, v/v) to give 13 (1.0 g, 1.8 mmol, 74%) as yellow foam. R$_f$=0.60 (5% methanol in dichloromethane, v/v). $^1$H NMR (600 MHz) δ: 8.52 (NH thymine), 7.81 (1H, s, H6 thymine), 6.88-7.34 (13H, m), 5.78 (1H, s, H1'), 4.31 (1H, s, H3'), 3.66 (1H, d, J$_{H5',H5''}$=12.6 Hz, H5"), 3.55 (1H, d, J$_{H5',H5''}$=12.6 Hz, H8'), 2.65 (1H, m, H7'), 2.4 (1H, d, J$_{H2',H3''}$=4.4 Hz, H2'), 2.04 (1H, dd, J$_{H6',H6''}$=12.3 Hz, J$_{H7',H6''}$=10.6 Hz, H6"), 1.89 (3H, d, J=1.3 Hz, thymine CH$_3$), 1.23 (3H, d, 7.3 Hz, CH$_3$—C7'), 1.17 (1H, dd, J$_{H6',H6''}$=12.3 Hz, J$_{H6',H7'}$=4.9 Hz, H6'); $^{13}$C NMR (600 MHz D$_2$O) δ: 164 (C4), 158.7, 149.8 (C2), 135.6, 135.7, 135.9 (aromatic), 130 (C6), 113.3, 127.1, 128, 128.1 (aromatic), 109.4 (C5), 89.3 (C4'), 84.1 (C1'), 73.1 (C3'), 61 (C5'), 55.2 (OCH$_3$), 50.4 (C2'), 37.4 (C6'), 28.5 (C7'), 15.3 (C7'-methyl), 12.3 (CH$_3$, thymine); MALDI-TOF m/z [M+H]$^+$ found 585.22, calcd 585.25.

(1R,3R,4R,5R,7S)-7-(2-(Cyanoethoxy-(diisopropylamino)-phosphinoxy)-1-(4,4'-dimethoxytrityloxy methyl)-3-(thymin-1-yl)-2-oxa-bicyclo[2.2.1]heptane (14). Compound 13 (0.5 g, 0.85 mmol) was dissolved in 6 mL dry THF, DIPEA (0.57 mL, 0.2 mmol) was added at 0° C. followed by 2-cyanoethyl N,N-diisopropylphosphoramidochloridite (0.4 mL, 1.7 mmol) and reaction stirred overnight at room temperature. Methanol (0.5 mL) was added followed by aqueous saturated NaHCO$_3$ and extracted twice (25 mL) with dichloromethane. The organic phase was dried, evaporated and chromatographed on silica gel (1% Et$_3$N, ethyl acetate in cyclohexane, v/v) to give 14 (0.5 g, 80%) as a mixture of 4 isomers; $^{31}$P NMR (109.4 MHz, CDCl$_3$):148.82, 149.19, 149.36, 150.08. The four signals in $^{31}$P NMR have been integrated and are found to be in the ratio of 7:3 as found in the $^1$H NMR spectrum of 12a/12b. The integration is included in the SI (Inset in FIG. S42). MALDI-TOF m/z [M+H]$^+$ found 785.67, calcd 785.36.

3,5-Di-O-benzyl-4-C-hydroxypropyl-1,2-O-isopropylidine-α-D-ribofuranose (15)

A 0.5 Molar solution of 9-BBN (88 mL, 44 mmol) was added dropwise to a solution of 6 (6 g, 14 mmol) in dry THF (100 mL) and stirred overnight. Water was added till gas evolution stops, 3N NaOH solution (25 mL) was then added and slowly 33% aqueous $H_2O_2$ was added while temperature was maintained at not more than 50° C. the mixture was stirred for about 30 min at room temperature and then partitioned between ethyl acetate and water and extracted twice with ethyl acetate (100 mL) the organic layer was dried evaporated and purified over silica gel (30-35% ethyl acetate in cyclohexane, v/v) to give 15 as colourless oil (5.4 g, 13 mmol, 90%); $R_f$=0.40 (50% ethyl acetate in cyclohexane, v/v).$^1$H NMR (270 MHz CDCl$_3$) δ: 7.32 (10H, m, benzyl) 5.75 (1H, $J_{H1,H2}$=4 Hz, H1) 4.76 (1H, d, $J_{gem}$=12.1 Hz, CH$_2$Bn), 4.62 (1H, app t, 4.6 Hz, H2), 4.6 (1H, d, $J_{gem}$=12.3 Hz, CH$_2$Bn), 4.52 (1H, d, $J_{gem}$=12.3 Hz, CH$_2$Bn), 4.52 (1H, d, $J_{gem}$=12 Hz, CH$_2$Bn) 4.41 (1H, d, $J_{gem}$=12 Hz, CH$_2$Bn), 4.15 (1H, d, J=5.3 Hz, H3), 3.83 (2H, m, H8, 8'), 3.49 (1H, d, $J_{H5',H5''}$=10.3 Hz, H5'), 3.3 (1H, d, 10.3 Hz, H5''), 2.95 (2H, m, H6', H7') 1.72 (2H, m, H6'', 7''), 1.60 (3H, CH$_3$), 1.31 (3H, CH$_3$); $^{13}$C NMR (67.9 MHz) δ: 138.1, 128.4, 127.9, 127.7, 127.6, 113.1 (aromatic), 104.1 (C1), 87.1 (C4), 79.1 (C2), 78.6 (C3), 73.5 (CH$_2$Bn), 72.5 (CH$_2$Bn), 72.4 (C5), 62.7 (C8), 27.8 (C7), 26.9 (C6), 26.5 (CH$_3$), 26.0 (CH$_3$); MALDI TOF-m/z [M+Na]$^+$ found 451.12, calcd 451.2.

3,5-Di-O-benzyl-4-C-penten-yl-1,2-O-isopropylidine-α-D-ribofuranose (17)

Oxalyl chloride (2.48 mL, 29.20 mmol) was added to dichloromethane (100 mL) cooled at −78° C. DMSO (3.3 mL, 46.72 mmol) was added dropwise to this solution in about 30 min. After stirring for 20 more min a solution of 2 (5 g, 11.68 mmol) in dichloromethane (50 mL) was added dropwise to this mixture in about 20 min and left to stir at −78° C. for another 45 min. DIPEA (13 mL, 100 mmol) was added to this cooled mixture and allowed to warm to room temperature. Water was added to the reaction and twice extracted with dichloromethane (100 mL). The organic layer was washed with water and brine dried over MgSO$_4$ and concentrated under reduced pressure. In another reaction BuLi (1.6 molar solution in hexane, 22 mL, 35 mmole) was added to a pre-cooled suspension of methyl-triphenylphosphonium bromide (12.5 g, 35 mmol) at 0° C. in dry THF and allowed to stir at room temperature for 1 h. The yellow solution so obtained was cooled to −78° C. and a solution of crude aldehyde in dry THF was then added dropwise in about 20 min and left to stir at −78° C. overnight. The reaction was quenched with saturated aqueous NH$_4$Cl, and stirred for about 1 h at room temperature and then extracted with ether (3×100 mL) dried over MgSO$_4$ and concentrated under reduced pressure. The crude material was purified by column chromatography on silica gel (0-10% ethyl acetate in cyclohexane, v/v) to give 17 as yellowish oil (3.5 g, 8.4 mmoles, 72%). $R^f$=0.40 (30% ethyl acetate in cyclohexane, v/v). $^1$H NMR (270 MHz, CDCl$_3$) δ: 7.35 (10H, m), 5.84 (1H, m, H8), 5.76 (1H, d, $J_{H1,H2}$=4 Hz, H1), 4.95 (2H, m, H9, 9'), 4.80 (1H, d, $J_{gem}$=12.1 Hz, CH$_2$Bn), 4.62 (1H, app t, J=4.5 Hz, H2), 4.60 (1H, d, $J_{gem}$=12.1 Hz, CH$_2$Bn), 4.53 (1H, d, $J_{gem}$=11.9 Hz, CH$_2$Bn), 4.4 (1H, d, $J_{gem}$=12 Hz, CH$_2$Bn), 4.15 (1H, d, $J_{H2,H3}$=5.2 Hz, H3), 3.51 (1H, d, $J_{H5,H5'}$=10.3 Hz, H5), 3.31 (1H, d, $J_{H5,H5'}$=10.3 Hz, H5'), 2.35 (2H, m, H6 and H6'), 2.1 (1H, m, H7'), 1.70 (1H, m, H7'), 1.62 (3H, s, CH$_3$), 1.33 (3H, s, CH$_3$); $^{13}$C NMR (67.9 MHz) δ: 139.1 (C8), 138.2, 128.4, 127.8, 127.7 (aromatic), 114.2 (C9), 113.1, 104.1 (C1), 86.7 (C4), 79.3 (C2), 78.7 (C3), 73.5 (CH$_2$Bn), 72.8 (C5), 72.4 (CH$_2$Bn) 30.9 (C7), 27.8 (C6), 26.70 (CH$_3$), 26.3 (CH$_3$).

1-[3,5-Di-O-benzyl-4-C-penten-yl-2-hydroxy-β-D-ribofuranosyl]-thymine (20)

Acetic anhydride (9.5 mL, 50 mmol) and acetic acid (50 mL) was added to 4 (3.5 g, 8.2 mmol) and cooled on ice bath, triflic acid (0.03 mL, 0.4 mmol) was added to it and stirred. After 30 min the reaction was quenched with cold saturated NaHCO$_3$ solution and extracted with dichloromethane. The organic layer dried and evaporated. The crude was co-evaporated with dry CH$_3$CN thrice and dissolved in the same. Thymine (1.5 g, 12.37 mmol) and N,O-bis(trimethylsilyl)acetamide (5.0 mL, 24.75 mmol) were added to this solution and refluxed for 45 min till suspension becomes a clear solution. This solution was cooled to 0° C. and TMSOTf (1.71 mL, 9.9 mmol) was added dropwise and left to stir overnight. The reaction was quenched with saturated NH$_4$Cl solution and extracted with dichloromethane. The organic layer was dried, evaporated and treated with 27% methanolic ammonia overnight. After completion of reaction the solvent was evaporated and residue purified over silica gel (0-3% methanol in dichloromethane, v/v) to give 21 as a white foam (2.8 g, 5.77 mmol, 70% in three steps). $R_f$=0.50 (5% methanol in dichloromethane, v/v). $^1$H NMR (270 MHz, CDCl$_3$) δ: 7.51 (1H, s, H-6), 7.3 (10H, m, benzyl), 6.00 (1H, d, 5.44 Hz, H1'), 5.76 (1H, m, H8'), 4.94 (2H, m, H9' and H9''), 4.84 (1H, d, $J_{gem}$=11.8 Hz, CH$_2$Bn), 4.58 (1H, d, $J_{gem}$=11.8 Hz, CH$_2$Bn), 4.52 (1H, d, $J_{gem}$=12 Hz, CH$_2$Bn), 4.48 (1H, d, $J_{gem}$=12 Hz, CH$_2$Bn), 4.41 (1H, app t, J=5.6 Hz, H2'), 4.15 (1H, d, $J_{H2',H3'}$=5.8 Hz, H3'), 3.69 (1H, d, $J_{H5',H5''}$=9.9 Hz, H5''), 3.41 (1H, d, $J_{H5',H5''}$=9.9 Hz, H5'), 2.22 (1H, m, H6'), 2.04 (2H, m, H7' and H7''), 1.63 (1H, m, H6'), 1.49 (3H, thymine CH$_3$); $^{13}$C NMR (67.9 MHz, CDCl$_3$) δ: 164.2 (C2), 151.4 (C4), 138.5 (C8'), 136 (C6), 137.4, 130.0, 128.7, 128.5, 128.1, 127.7 (aromatic), 114.6 (C9'), 111.0 (C5), 88.8 (C1'), 87.3 (C4'), 79.1 (C3'), 75.1 (C2'), 73.3 (C5'), 73.6 (CH$_2$Bn), 73.4 (CH$_2$Bn), 31.9 (C6'), 27.7 (C7'), 12.1 (CH$_3$, thymine); MALDI TOF-m/z [M+H]$^+$ found 493.11, calcd 493.17.

1-[3,5-Di-O-benzyl-4-C-penten-yl-2-O-phenoxythiocarbonyl-β-D-ribofuranosyl]-thymine (21)

The nucleoside 20 (2.8 g, 5.7 mmol) was evaporated thrice with dry pyridine and dissolved in the same. To this pre-cooled solution was added DMAP (0.69 g, 5.7 mmol) and then dropwise was added phenyl chlorothionoformate (1.15 mL, 8.55 mmol) and reaction stirred overnight. Reaction was quenched with saturated solution of NaHCO$_3$ and extracted with dichloromethane. Organic layer was dried over MgSO$_4$ concentrated and chromatographed over silica gel (10-30% ethyl acetate in cyclohexane, v/v) to give 21 as yellowish foam (2.1 g, 3.42 mmol, 60%). $R_f$=0.60 (30% ethyl acetate in cyclohexane, v/v). $^1$H NMR (600 MHz, CDCl$_3$) δ: 8.32 (1H, br s, NH), 7.48 (1H, s, H6), 7.48-6.99 (15H, m), 6.4 (1H, d, $J_{H1',H2'}$=6.3 Hz, H1'), 5.94 (1H, app t, J=6.0 Hz, H2'), 5.77 (1H, m, H8'), 4.97 (2H, m, H9' and H9''), 4.77 (1H, d, $J_{gem}$=12 Hz, CH$_2$Bn), 4.55 (3H, d, $J_{gem}$=12 Hz, CH$_2$Bn), 4.53 (1H, d, $J_{H2',H3'}$=5.8 Hz, H3'), 3.74 (1H, d, $J_{H5',H5''}$=9.9 Hz, H5''), 3.47 (1H, d, $J_{H5',H5''}$=9.9 Hz, H5'), 2.22 (1H, m, H7'), 2.06 (1H, m, H7''), 1.94 (1H, m, H6'), 1.66 (1H, m, H6''), 1.53 (3H, thymine CH$_3$); $^{13}$C NMR (125.7 MHz, CDCl$_3$) δ: 194.4 (C=S), 163.3 (C4), 153.3, 150.2 (C2), 138.1 (C8'), 137.3, 137.0, 135.6 (C6), 129.5-121.9 (aromatic), 114.8 (C9'), 111.5 (C5), 87.6 (C4'), 85.1 (C1'), 82.9 (C2'), 78.1 (C3'), 74.9 (CH$_2$Bn), 73.7 (C5'), 73.6 (CH$_2$Bn), 31.6 (C6'), 27.6 (C7'), 12.0 (CH$_3$ thymine); MALDI-TOF m/z [M+H]$^+$ found 629.09, calcd 629.73.

(1R,2R,5R,7R,8S)-8-Benzyloxy-5-benzyloxymethyl-7-(thymin-1-yl)-6-oxa-bicyclo[3.2.1]octane (22)

(2.1 g, 3.3 mmol) of 21 was dissolved in 200 mL of dry toluene and purged for 30 min and then put to reflux Bu$_3$SnH (0.8 mL, 3.0 mmol) dissolved in 25 mL of dry toluene was added dropwise to this solution and refluxed for 15 min. AIBN (0.768 g, 4 mmol) was dissolved in dry toluene and added dropwise to the refluxing solution over 60 min, simultaneously was added Bu$_3$SnH (0.8 mL, 3.3 mmol) dissolved in 25 mL of dry toluene and reaction left at reflux till starting material is exhausted in about 60 more min. The reaction was cooled and 25 mL of CCL$_4$ was added followed by addition of solution of iodine dissolved in ether till the color persists, the solvent was evaporated over vacuum and residue taken in diethyl ether and repeatedly washed with saturated solution of potassium fluoride. The ether layer is dried evaporated and chromatographed over silica gel (0-20% ethylacetate in cyclohexane, v/v) to give 22 as white powder (1.19 g, 2.5 mmol, 76%). R$_f$=0.40 (30% ethyl acetate in cyclohexane, v/v). $^1$H NMR (600 MHz, CDCl$_3$) δ: 8.71 (1H, br s, NH), 8.06 (1H, s, H6), 7.3 (10H, m), 5.82 (1H, s, H1'), 4.56 (2H, dd, J$_{gem}$=10.8 Hz, CH$_2$Bn), 4.54 (1H, d, J$_{gem}$=10.8 Hz, CH$_2$Bn), 4.47 (1H, d, J$_{gem}$=10.8 Hz, CH$_2$Bn), 4.17 (1H, d, J$_{H2',H3'}$=5.4 Hz, H3'), 3.69 (1H, d, J$_{H5',H5''}$=10.8 Hz, H5'), 3.55 (1H, d, J$_{H5',H5''}$=10.8 Hz, H5''), 2.31 (1H, d, J$_{H2',H3'}$=4.8 Hz, H2'), 2.22 (1H, m, H8'), 1.83 (1H, m, H7), 1.66 (1H, m, H6''), 1.43 (3H, s, CH$_3$ thymine), 1.33 (2H, m, H6', H7''), 1.11 (3H, J$_{CH3,H8'}$=7.2 Hz, CH$_3$—C8'); $^{13}$C NMR (125.7 MHz, CDCl$_3$) δ: 164.1 (C4), 149.9 (C2) 137.4, 136.6 (C6), 128.5, 128.3, 128.0, 127.8, 127.3, 109.1 (C5), 84.7 (C1'), 84.6 (C4'), 73.5 (C3'), 73.51 (CH$_2$Bn), 71.7 (CH$_2$Bn), 70.6 (C5'), 48.4 (C2'), 27.0 (C6'), 26.5 (CT), 25.6 (C8'), 18.9 (C8', methyl), 11.8 (CH$_3$, thymine); MALDI-TOF m/z [M+H]$^+$ found 477.56, calcd 477.39.

(1R,2R,5R,7R,8S)-8-Hydroxy-5-hydroxymethyl-7-(thymin-1-yl)-6-oxa-bicyclo[3.2.1]octane (23)

Compound 22 (1.2 g, 2.5 mmol) was dissolved in dry methanol. 20% Pd(OH)$_2$/C (1.3 g), ammonium formate (3.4 g, 50 mmol) were added and put to reflux. Same amount of ammonium formate and 20% Pd(OH)$_2$/C was added thrice after every 3 h and reaction left to reflux overnight. After the reaction was finished as seen by TLC the suspension was filtered over celite and organic phase evaporated and chromatographed over silica gel (2-7% methanol in dichloromethane, v/v) to give 25 as white powder (0.60 g, 2.0 mmol, 82%). R$_f$=0.50 (10% methanol in dichloromethane, v/v). $^1$H NMR (600 MHz, D$_2$O) δ: 8.19 (1H, s, H6), 5.77 (1H, s, H1'), 4.25 (1H, d, J$_{H2',H3'}$=5.2 Hz, H3'), 3.71 (2H, s, H5' and H5''), 2.26 (1H, d, J$_{H2',H3'}$=5.2 Hz, H2'), 2.20 (1H, m, H8'), 1.86 (3H, s, CH$_3$-thymine), 1.68 (1H, m, H6), 1.36 (1H, m, H7'), 1.25 (2H, m, H7'', H6''), 1.05 (3H, d, J$_{CH3,H8'}$=7 Hz, C8'-CH$_3$); $^{13}$C NMR (125.7 MHz, CDCl$_3$) δ: 165.0 (C4), 150.8 (C2), 137.4 (C6), 108.0 (C5), 86.0 (C4'), 84.2 (C1'), 65.5 (C3'), 62.3 (C5'), 51.6 (C2'), 27.3 (C6'), 26.6 (C7'), 25.5 (C8'), 19.9 (C8'-CH$_3$), 13.3 (CH$_3$, thymine); MALDI-TOF m/z [M]$^+$ found 296.97, calcd 296.14.

(1R,2R,5R,7R,8S)-5-(4,4'-Dimethoxytrityloxymethyl)-8-hydroxy-7-(thymin-1-yl)-6-oxa-bicyclo[3.2.1]octane (24)

Compound 23 (0.5 g, 1.68 mmol) was evaporated twice with dry pyridine and then suspended in the same. 4,4'-dimethoxytrityl chloride was added and stirred at room temperature overnight. Reaction was quenched with aqueous NaHCO$_3$ and extracted with dichloromethane. The organic layer was dried, evaporated and chromatographed on silica gel (1% pyridine, ethyl acetate in cyclohexane, v/v) to give 26 (0.8 g, 1.34 mmol, 80%) as yellowish foam. R$_f$=0.60 (30% ethyl acetate in cyclohexane, v/v). $^1$H NMR (600 MHz, CDCl$_3$+DABCO) δ: 7.8 (1H, s, H6), 6.83-7.4 (13H, m), 5.77 (1H, s, H1'), 4.44 (1H, d, J$_{H2',H3'}$=5.2 Hz, H3'), 3.78 (6H, s, 2×OCH$_3$), 3.36 (1H, d, J$_{H5',H5''}$=10.6 Hz, H5'), 3.26 (1H, d, J$_{H5',H5''}$=10.6 Hz, H5''), 2.30 (1H, m, H8'), 2.27 (1H, d, J$_{H2',H3'}$=5.2 Hz, H2'), 1.77 (1H, m, H6''), 1.64 (1H, m, H7'), 1.36 (1H, m, H7''), 1.25 (2H, m, H6' and H7), 1.1 (3H, d, J$_{H8',CH3}$=7 Hz, C8'-CH$_3$); $^{13}$C NMR (125.7 MHz) δ: 164.1 (C4), 158.6 (C2), 158.6, 149.9, 144.3, 135.9 (C6), 135.4, 135.3, 130.0, 128.1, 128.0, 127.1, 113.2, 109.4, 84.8 (C1'), 84.8 (C4'), 67.9 (C3'), 54.5 (C5'), 55.2 (OCH$_3$), 50.8 (C2'), 46.9 (DABCO), 26.9 (C7'), 26.4 (C6'), 25.0 (C8'), 18.9 (C8'-CH$_3$), 11.9 (CH$_3$, thymine); MALDI-TOF m/z [M+Na]$^+$ found 621.59, calcd 621.29.

(1R,2R,5R,7R,8S)-8-(2-(Cyanoethoxy(diisopropylamino)-phosphinoxy)-5-(4,4'-dimethoxytrityloxymethyl)-7-(thymin-1-yl)-6-oxa-bicyclo[3.2.1]octane (25)

Compound 24 (0.5 g, 0.83 mmol) was dissolved in 6 mL of dry THF, diisopropylethylamine (0.75 mL, 4.18 mmol) was added and reaction cooled in ice bath. To this was added 2-cynoethyl N,N-diisopropylphosphoramidochloridite (0.36 mL, 1.66 mmol) and stirred overnight at room temperature. Reaction was quenched by addition of cold aqueous NaHCO$_3$ and extracted with dichloromethane. The organic layer dried, evaporated and chromatographed over silica gel (1% Et$_3$N, ethyl acetate in cyclohexane, v/v) to give 27 (0.55 g, 0.7 mmol 84%); $^{31}$P NMR (109.4 MHz, CDCl$_3$) δ 149.25, 150.26; MALDI-TOF m/z [M+H]$^+$ found 799.64, calcd 799.9.

UV Melting Experiments.

All 17 modified AONs have been purified as a single component on PAGE (20% polyacrylamide with 7 Molar urea), extracted with 0.3 M NaOAc and desalted with C-18 reverse phase cartridge to give AONs in >99% purity and correct mass have been obtained by MALDI-TOF mass spectroscopy for each one them (Table 1). Determination of the T$_m$ of the AON/RNA hybrids was carried out in the following buffer: 57 mM Tris-HCl (pH 7.5), 57 mM KCl, 1 mM MgCl$_2$. Absorbance was monitored at 260 nm in the temperature range from 20° C. to 90° C. using UV spectrophotometer equipped with Peltier temperature programmer with the heating rate of 1° C. per minute. Prior to measurements, the samples (1 μM of AON and 1 μM RNA mixture) were pre-annealed by heating to 90° C. for 5 min followed by slow cooling to 4° C. and 30 min equilibration at this temperature and are average of at least three independent runs.

$^{32}$P Labeling of Oligonucleotides.

The oligoribonucleotide, oligodeoxyribonucleotides were 5'-end labeled with $^{32}$P using T4 polynucleotide kinase, [γ-$^{32}$P]ATP and standard protocol.[71] Labeled AONs and the target RNA were purified by 20% denaturing PAGE and specific activities were measured using Beckman LS 3801 counter.

Exonuclease Degradation Studies.

Stability of the AONs toward 3'-exonucleases was tested using snake venom phosphodiesterase (SVPDE) from Crotalus adamanteus. All reactions were performed at 3 μM DNA concentration (5'-end $^{32}$P labeled with specific activity 80 000 cpm) in 56 mM Tris-HCl (pH 7.9) and 4.4 mM MgCl$_2$ at 21°

C. Exonuclease concentration of 17.5 ng/μL was used for digestion of oligonucleotides. Total reaction volume was 14 μL. Aliquots were taken at 1, 2, 24, 48 and 72 h and quenched by addition of the same volume of 50 mM EDTA in 95% formamide. Reaction progress was monitored by 20% denaturing (7 M urea) PAGE and autoradiography.

Stability Studies in Human Serum.

AONs (6 μL) at 2 μM concentration (5'-end $^{32}$P labeled with specific activity 80 000 cpm) were incubated in 26 μL of human blood serum (male AB) at 21° C. (total reaction volume was 36 μL) and the experiments were repeated twice up to 48 h. Aliquots (3 μL) were taken at 0, 30 min, 1, 2, 5, 7, 8, 9, 12, 24, 36, 48 h and quenched with 7 μL of solution containing 8 M urea and 50 mM EDTA, resolved in 20% polyacrylamide denaturing (7 M urea) gel electrophoresis and visualized by autoradiography. The $^{32}$P label at the 5'-terminal were cleaved gradually by the phosphatases present in the blood serum, which resulted in lower radioactive count as the digestion progressed with time. Since no new prominent cleavage products were found toward the later time points, we considered those prominent stable initial fragments as 100% during the last time points (12-48 h).

Theoretical Calculations.

Carbocyclic analogs of the ENA and LNA nucleosides have been investigated in silico using ab initio and molecular dynamics techniques. Their molecular structures have been refined using Amber force field and available structural information from NMR experiments according to the following protocol: (i) Derive initial dihedral angles from the observed $^3J_{H,H}$ using Haasnoot-de Leeuw-Altona generalized Karplus equation; (ii) Perform NMR constrained molecular dynamics (MD) simulation (0.5 ns, 10 steps) simulated annealing (SA) followed by 0.5 ns NMR constrained simulations at 298 K using the NMR derived torsional constraints from Step (i) to yield NMR defined molecular structures; (iii) Acquire 6-31G** Hartree-Fock optimized ab initio gas phase geometries in order to compare the experimentally derived torsions with the ab initio geometry; (iv) Analyze the full conformational hyperspace using 2 ns NMR/ab initio constrained MD simulations of compounds 12a, 12b and 23 followed by full relaxation of the constraints.

The geometry optimizations of the modified nucleosides have been carried out by GAUSSIAN 98 program package at the Hartree-Fock level using 6-31G** basis set. The atomic charges and optimized geometries of compounds 12a, 12b, and 23 were then used as AMBER[87] force field parameters employed in the MD simulations. The protocol of the MD simulations is based on Cheatham-Kollman's[88] procedure employing modified version of Amber 1994 force field as it is implemented in AMBER 7 program package.[87] Periodic boxes containing 718 (12a,12b) and 753 (23) TIP3P[89] water molecules to model explicit solvent around the compounds, were generated using xleap extending 12.0 Å from these molecules in three dimensions in both the NMR constrained and unconstrained MD simulations. SA protocol included ten repeats of 25 ps heating steps from 298 K to 400 K followed by fast 25 ps cooling steps from 400 K to 298 K. During these SA and NMR constrained MD simulations torsional constraints of 50 kcal mol$^{-1}$rad$^{-2}$ were applied. The constraints were derived from the experimental $^3J_{H2',H3'}$ and available $^3J_{H2',H7'/H8}$ coupling constants using Haasnoot-de Leeuw-Altona generalized Karplus equation.[66, 67] Ten SA repeats were followed by 0.5 ns MD run at constant 298 K temperature applying the same NMR constraints.

Generalized Karplus Parameterization.

Relevant vicinal proton $^3J_{H,H}$ coupling constants have been back-calculated from the corresponding theoretical torsions employing Haasnoot-de Leeuw-Altona generalized Karplus equation[66,67] taking into account β substituent correction in form:

$$^3J = P_1 \cos^2(\phi) + P_2 \cos(\phi) + P_3 + \Sigma(\Delta_{\chi i}^{group}(P_4 + P_5 \cos^2(\xi_i \phi + P_6|\Delta_{\chi i}^{group}|)))$$

where $P_1$=13.70, $P_2$=−0.73, $P_3$=0.00, $P_4$=0.56, $P_5$=−2.47, $P_6$=16.90, $P_7$=0.14 (parameters from.[66]), and $\Delta_{\chi i}^{group}$ = $\Delta_{\chi i}^{\alpha\text{-}substituent} - P_7 \Sigma \Delta_{\chi i}^{\beta\text{-}substituent}$ where $\Delta_{\chi i}$ are taken as Huggins electronegativities.[90]

Acknowledgements

Generous financial support from the Swedish Natural Science Research Council (Vetenskapsrådet), the Swedish Foundation for Strategic Research (Stiftelsen för Strategisk Forskning) and the EU-FP6 funded RIGHT project (Project no. LSHB-CT-2004-005276) is gratefully acknowledged. We would like to thank Mr. O. P. Varghese for providing aza-ENA-T modified AONs for this study. Puneet Srivstava (PS) has planned and carried through total synthesis of carbocyclic nucleosides, their incorporations into oligos, enzymology, physicochemical studies and NMR characterization. Malgorzata Wenska was responsible for the scale up of compound 23 using PS's procedure. Jharna Barman has performed enzymological experiments with PS. Wimal Pathmasiri has performed detailed NMR characterization by 500/600 MHz NMR and simulation. Oleksandr Plashkevych has performed molecular structure analysis based on the NMR experiments and ab initio and MD simulations.

Supporting Information Available:

$^1$H and $^{13}$C NMR spectra of compounds 2-17 and 20-24; $^{31}$P NMR of compounds 14 and 25; 1D nOe of 12a/12b and 23; DEPT spectra of compounds 12a/12b and 23; COSY spectra of 12a/12b and 23; TOCSY spectra of 12a/12b and 23; HMQC spectra of 10, 11a/11b, 12a/12b, 21, 22 and 23; HMBC spectra of 10, 11a/11b, 12a/12b, 21, 22 and 23; $^3J_{HH}$ Simulations of compounds 12a/12b and 23; Plots of percentage remaining of AONs 6-17 in human blood serum with time; SVPDE digestion profile of AONs 1-17 (denaturing PAGE autoradiograms); Plots of percentage remaining of AONs 6-17 in SVPDE; Correlation of experimental $^3J_{H1',H2'}$ and $^3J_{H2',H3'}$ vicinal coupling constants in carbocyclic-ENA-T (12a, 12b) and carbocyclic LNA-T (23) as well as their 2'-O— and 2'-N— analogs (ENA-T, aza-ENA-T, LNA-T and 2'-amino-LNA-T); Overlay of 2500 molecular structures of the carbocyclic-ENA-T nucleoside collected every 0.2 ps of the last 500 ps (1.5-2.0 ns) of its MD simulation and their analysis; Tables of $^1$H chemical shifts and $^3J_{HH}$ coupling constants for compounds 11, 12a/12b, 22 and 23; Table of experimental and theoretical $^3J_{HH}$ vicinal coupling constants and Tables of sugar torsions, pseudorotational phase angle, sugar puckering amplitude and Solvation energy ($E_{solv}$) calculated using Baron and Cossi's implementation of the polarizable conductor CPCM model.[85] and a complete discussion of structure assignment of bicyclic system for compounds 12a/12b and 23 as well as their molecular structures based on NMR, ab initio and MD calculations are available in SI.

REFERENCES

1. Zamecnik, P. C.; Stephenson, M. L., *Proc. Natl. Acad. Sci. USA* 1978, 75, 280-284.
2. Crooke, S. T., *Annu. Rev. Med.* 2004, 55, 61-95.
3. Buchini, S.; Leumann, C. J., *Curr. Opin. Chem. Biol.* 2003, 7 (6), 717-726.
4. Montgomery, M. K.; Xu, S.; Fire, A., *Proc. Natl. Acad. Sci. USA* 1998, 95 (26), 15502-15507.

5. Kurreck, J., *Eur. J. Biochem.* 2003, 270, 1628-1644.
6. Freier, S. M.; Altmann, K. H., *Nucleic Acids Res.* 1997, 25, 4429-4443.
7. Eckstein, F., *Annu. Rev. Biochem.* 1985, 54, 367-402.
8. Holmlund, J. T., *Ann. NY Acad. Sci.* 2003, 1002 (Therapeutic Oligonucleotides), 244-251.
9. Leumann, C. J., *Bioorg. Med. Chem.* 2002, 10, 841-854.
10. Steffens, R.; Leumann, C., *Helv. Chim. Acta* 1997, 80, 2426-2439.
11. Wengel, J., *Acc. Chem. Res* 1999, 32, 301-310.
1. Koshkin, A. A.; Singh, S. K.; Nielsen, P.; Rajwanshi, V. K.; Kumar, R.; Meldgaard, M.; Olsen, C. E.; Wengel, J., *Tetrahedron* 1998, 54 (14), 3607-3630.
7. Morita, K.; Takagi, M.; Hasegawa, C.; Kaneko, M.; Tsutsumi, S.; Sone, J.; Ishikawa, T.; Imanishi, T.; Koizumi, M., *Bioorg. Med. Chem.* 2003, 11 (10), 2211-2226.
2. Obika, S.; Nanbu, D.; Hari, Y.; Morio, K.-I.; In, Y.; Ishida, T.; Imanishi, T., *Tetrahedron Lett.* 1997, 38 (50), 8735-8738.
3. Singh, S. K.; Kumar, R.; Wengel, J., *J. Org. Chem.* 1998, 63 (26), 10035-10039.
4. Pradeepkumar, P. I.; Cheruku, P.; Plashkevych, O.; Acharya, P.; Gohil, S.; Chattopadhyaya, J., *J. Am. Chem. Soc* 2004, 126, 11484-11499.
5. Honcharenko, D.; Varghese, O. P.; Plashkevych, O.; Barman, J.; Chattopadhyaya, J., *J. Org. Chem.* 2006, 71, 299-314.
6. Koizumi, M., *Curr. Opin. Mol. Ther.* 2006, 8, 144-149.
8. Varghese, O. P.; Barman, J.; Pathmasiri, W.; Plashkevych, O.; Honcharenko, D.; Chattopadhyaya, J., *J. Am. Chem. Soc* 2006, 128 (47), 15173-15187.
9. Babu, B. R.; Raunak; Poopeiko, N. E.; Juhl, M.; Bond, A. D.; Parmar, V. S.; Wengel, J., *Eur. J. Org. Chem.* 2005, 11, 2297-2321.
10. Rajwanshi, V. K.; Hakansson, A. E.; Sorensen, M. D.; Pitsch, S.; Singh, S. K.; Kumar, R.; Nielsen, P.; Wengel, J., *Angew. Chem., Int. Ed.* 2000, 39 (9), 1656-1659.
11. Morita, K.; Hasegawa, C.; Kaneko, M.; Tsutsumi, S.; Sone, J.; Ishikawa, T.; Imanishi, T.; Koizumi, M., *Bioorg. Med. Chem. Lett* 2001, 12 (1), 73-76.
12. Morita, K.; Yamate, K.; Kurakata, S.; Abe, K.; Imanishi, T.; Koizumi, M., *Nucleic Acids Res. Sup.* 2002, 2, 99-100.
13. Morita, K.; Yamate, K.; Kurakata, S.-I.; Watanabe, K.; Imanishi, T.; Koizumi, M., *Nucleosides, Nucleotides Nucleic Acids* 2003, 22, 1619-1621.
14. Albaek, N.; Petersen, M.; Nielsen, P., *J. Org. Chem.* 2006, 71 (20), 7731-7740.
15. Bakuzis, P.; Campos, O. O. S.; Bakuzis, M. L. F., *J. Org. Chem.* 1976, 41 (20), 3261-3264

We claim:

1. A ribonucleoside derivatives according to formula 1 or 2 as shown below:

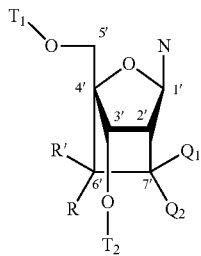

1

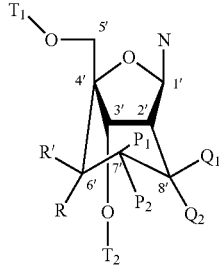

2 wherein N is a nucleobase moiety selected from the group consisting of:
-1-thyminyl-, -9-adeninyl-, -9-guaninyl-, -1-cytosinyl-, -5-methyl-1-cytosinyl-, -5-fluoro-1-cytosinyl-, -5-fluoro-1-cytosinyl- and -5-trifluoromethyl-1-uracilyl-, respectively, $T_1$ and/or $T_2$ selected from the group consisting of H, acetyl, benzyl, t-butyldimethysilyl, t-butyldiphenylsilyl, dimethoxytrital, 9-fluorenylmethoxycarbonyl, phosphate, phosphomonoester, phosphodiester, phosphotriester, phosphoramidite, phosphoramidate, phosphorothioate, or the reactive phosphorus group as in 2-cyanoethyl N,N-diisopropylphosphoramidite, H-phosphonate or methyl H-phosphonate, wherein in general formula 1 the ring is a 5-membered cis-fused carbocycle (fused at C4' and C2' of the β-D-pentofuranosyl ring of the ribo or arabino nucleoside or nucleotide) with substituents at C6' (R/R') and/or C7' ($Q_1/Q_2$), in any combination of either R or S configuration at any of those chiral/prochiral carbon-centers; wherein $Q_1$ is selected from the group consisting of —H, OH, F, methyl, $CF_3$, ethyl, propyl, butyl, pentyl, hexyl, substituted alkyl, trifluoromethoxy and trifluoroethoxy and $Q_2$=H, OH, F, methyl, $CF_3$, aryl, aryloxy, MeO, alkoxy, trifluoromethoxy, trifluoroethoxy, azido, amino, aminoalkyl, alkylamino, thioalkyl, alkylthio, alkoxymethyleneamino-, alkoxyethyleneamino-, aminoethylenealkoxy-, alkyl/aryl-aminoethylenealkoxy-, ureido, phosphate, phosphoroamidite, phosphorothioate, phosphonate, guanidino, NHMe or $NMe_2$, or $Q_1$ in combination with $Q_2$ and the carbon to which the are attached is a (C=O) group, a ($C=CH_2$) group, an oxime (C=NOH) or oxime-ether (C=NOJ), wherein J=methyl, ethyl, propyl, butyl, benzyl, methoxy benzyl or methylbenzyl, and with the provisos that when $Q_1$ is H, $Q_2$ is a substituent other than H, and when $Q_2$ is H, $Q_1$ is a substituent other than H;

and either R and/or R' is a substituent at C6' in R or S configuration;

wherein R=H, OH, F, methyl, $CF_3$, ethyl, propyl, butyl, pentyl, hexyl, substituted alkyl, trifluoromethoxy, trifluoroethoxy, aryl, aryloxy, MeO, alkoxy, azido, amino, aminoalkyl, alkylamino, thioalkyl, alkylthio, alkoxymethyleneamino-, alkoxyethyleneamino-, aminoethylenealkoxy-, alkyl/aryl-aminoethylenealkoxy-, ureido, phosphate, phosphoramidite, phosphorothioate, phosphonate, guanidino, NHMe or NMe$_2$, and R'=H, OH, F, methyl, CF$_3$, ethyl, propyl, butyl, pentyl, hexyl, substituted alkyl, trifluoromethoxy, trifluoroethoxy, aryl, aryloxy, MeO, alkoxy, azido, amino, aminoalkyl, alkylamino, thioalkyl, alkylthio, alkoxymethyleneamino-, alkoxyethyleneamino-, aminoethylenealkoxy-, alkyl/aryl-aminoethylenealkoxy-, ureido, phosphate, phosphoramidite, phosphorothioate, phosphonate, guanidino, NHMe or NMe$_2$, or R in combination with R' and the carbon to which they are attached is a (C=O) group, a (C=CH$_2$) group, an oxime (C=NOH) or oxime-ether (C=NOJ), wherein J=methyl, ethyl, propyl, butyl, benzyl and methoxy benzyl or methylbenzyl when, R=R'=H then one of the Q$_1$ or Q$_2$ is other than H, wherein in general formula 2 the ring is a 6-membered cis-fused carbocycle (fused at C4' and C2' of the β-D-pentofuranosyl ring of the ribo or arabino nucleoside or nucleotide) with substituents at C6' (R/R') and/or C7' (P$_1$/P$_2$) and/or C8' (Q$_1$/Q$_2$) in any combination of either R or S configuration at any of those chiral/prochiral carbon-centers;

wherein Q$_1$ is selected from the group consisting of =H, OH, F, methyl, CF$_3$, ethyl, propyl, butyl, pentyl, hexyl, substituted alkyl, trifluoromethoxy, trifluoroethoxy, aryl, aryloxy, MeO, alkoxy, azido, amino, aminoalkyl, alkylamino, thioalkyl, alkylthio, alkoxymethyleneamino-, alkoxyethyleneamino-, aminoethylenealkoxy-, alkyl/aryl-aminoethylenealkoxy-, ureido, phosphate, phosphoramidite, phosphorothioate, phosphonate, guanidino, NHMe and NMe$_2$;

and Q$_2$=H, OH, F, methyl, CF$_3$, ethyl, propyl, butyl, pentyl, hexyl, substituted alkyl, trifluoromethoxy, trifluoroethoxy, aryl, aryloxy, MeO, alkoxy, azido, amino, aminoalkyl, alkylamino, thioalkyl, alkylthio, alkoxymethyleneamino-, alkoxyethyleneamino-, aminoethylenealkoxy-, alkyl- or aryl-aminoethylenealkoxy-, ureido, phosphate, phosphoramidite, phosphorothioate, phosphonate, guanidino, NHMe or NMe$_2$, or Q$_1$ in combination with Q$_2$ and the carbon to which they are attached is a (C=O) group, a (C=CH$_2$) group, an oxime (C=NOH) or oxime-ether (C=NOJ), wherein J=methyl, ethyl, propyl, butyl, benzyl, methoxy benzyl or methylbenzyl, (ii) with the provisos that when Q$_1$ is H, Q$_2$ is a substituent other than H, and when Q$_2$ is H, Q$_1$ is a substituent other than H;

and R=H, OH, F, methyl, CF$_3$, methyl, propyl, butyl, pentyl, hexyl, substituted alkyl, trifluoromethoxy, trifluoroethoxy, aryl, aryloxy, MeO, alkoxy, azido, amino, aminoalkyl, alkylamino, thioalkyl, alkylthio, alkoxymethyleneamino-, alkoxyethyleneamino-, aminoethylenealkoxy-, alkyl- or aryl-aminoethylenealkoxy-, ureido, phosphate, phosphoramidite, phosphorothioate, phosphonate, guanidine, NHMe or NMe$_2$;

and R'=H, OH, F, methyl, CF$_3$, ethyl, propyl, butyl, pentyl, hexyl, substituted alkyl, trifluoromethoxy, trifluoroethoxy, aryl, aryloxy, MeO, alkoxy, azido, amino, aminoalkyl, alkylamino, thioalkyl, alkylthio, alkoxymethyleneamino-, alkoxyethyleneamino-, aminoethylenealkoxy-, alkyl/aryl-aminoethylenealkoxy-, ureido, phosphate, phosphoramidite, phosphorothioate, phosphonate, a guanidino, NHMe or NMe$_2$, or R in combination with R' and the carbon to which they are attached is a (C=O) group, a (C=CH$_2$) group, an oxime (C=NOH) or oxime-ether (C=NOJ), wherein J=methyl, ethyl, propyl, butyl, benzyl methoxy benzyl or methylbenzyl, and P$_1$=H, OH, F, methyl, CF$_3$, ethyl, propyl, butyl, pentyl, hexyl, substituted alkyl, trifluoromethoxy, trifluoroethoxy, aryl, aryloxy, MeO, alkoxy, azido, amino, aminoalkyl, alkylamino, thioalkyl, alkylthio, alkoxymethyleneamino-, alkoxyethyleneamino-, aminoethylenealkoxy-, alkyl- or aryl-aminoethylenealkoxy-, ureido, phosphate, phosphoramidite, phosphorothioate, phosphonate, guanidino, NHMe or NMe$_2$, and P$_2$=H, OH, F, methyl, CF$_3$, ethyl, propyl, butyl, pentyl, hexyl, substituted alkyl, trifluoromethoxy, trifluoroethoxy, aryl, aryloxy, MeO, alkoxy, azido, amino, aminoalkyl, alkylamino, thioalkyl, alkylthio, alkoxymethyleneamino-, alkoxyethyleneamino-, aminoethylenealkoxy-, alkyl/aryl-aminoethylenealkoxy-, ureido, phosphate, phosphoramidite, phosphorothioate, phosphonate, guanidino, NHMe, or NMe$_2$, or P$_1$ in combination with P$_2$ and the carbon to which they are attached is a (C=O) group, a (C=CH$_2$) group, an oxime (C=NOH) or oxime-ether (C=NOJ), wherein J=methyl, ethyl, propyl, butyl, benzyl methoxy benzyl or methylbenzyl, with the proviso that when each of R, R', P$_1$ and P$_2$ is H, then one of Q$_1$ or Q$_2$ is other then H.

2. A nucleoside derivative having one of formulas 14a, 14b or 25 as defined below:

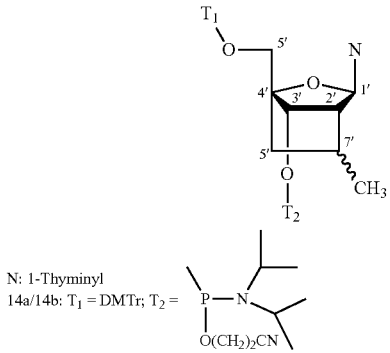

Scheme 1

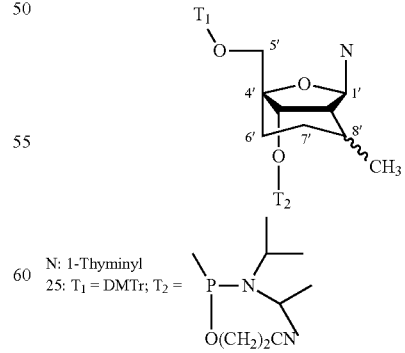

Scheme 2 wherein in Scheme 1, the C7' center, and in Scheme 2 the C8' center is in either the R or S configuration, and wherein N in both Schemes 1 and 2 the derivative is in the beta-D-configuration.

3. A 2'-deoxyoligoribonucleotide sequence or an oligoribonucleotide sequence comprising one or more 3'-phosphate, 5'-phosphate, 3'-phosphorothioate, or 5'-phosphorothioate derived monomeric unit(s) selected from phosphorylated and phosphorothiolated derivatives of the nucleoside precursors of compounds 14a, 14b and 25 as defined in claim 2.

4. The nucleoside derivative of claim 1, wherein N is 1-thyminyl.

5. A composition comprising a 2'-deoxyribo- or ribo-oligonucleotide sequence of claim 3 and a pharmaceutically compatible carrier.

* * * * *